United States Patent
Manolidis

(10) Patent No.: US 12,161,573 B2
(45) Date of Patent: Dec. 10, 2024

(54) STENT AND STENT DELIVERY FOR VASCULAR SURGERY

(71) Applicant: Spiros Manolidis, Southlake, TX (US)

(72) Inventor: Spiros Manolidis, Southlake, TX (US)

(73) Assignee: Tensor Flow Ventures LLC, Dallas, TX (US)

( * ) Notice: Subject to any disclaimer, the term of this patent is extended or adjusted under 35 U.S.C. 154(b) by 454 days.

(21) Appl. No.: 16/752,265

(22) Filed: Jan. 24, 2020

(65) Prior Publication Data

US 2020/0237539 A1 Jul. 30, 2020

Related U.S. Application Data

(63) Continuation-in-part of application No. 16/752,343, filed on Jan. 24, 2020, and a continuation-in-part of
(Continued)

(51) Int. Cl.
*A61F 2/90* (2013.01)
*A61B 5/00* (2006.01)
(Continued)

(52) U.S. Cl.
CPC .............. *A61F 2/966* (2013.01); *A61B 5/026* (2013.01); *A61B 5/6862* (2013.01); *A61F 2/848* (2013.01);
(Continued)

(58) Field of Classification Search
CPC .... A61F 2/966; A61F 2/88; A61F 2/90; A61F 2002/8483; A61F 2002/8486;
(Continued)

(56) References Cited

U.S. PATENT DOCUMENTS 4,054,128 A   10/1977 Seufert et al.
4,832,055 A *  5/1989 Palestrant ............ A61F 2/0105
                                                    128/899
(Continued)

FOREIGN PATENT DOCUMENTS

CN   104116484 A1   10/2014
DE   102016007669 A1   12/2017
(Continued)

OTHER PUBLICATIONS

International Preliminary Report on Patentability for International Application No. PCT/US2020/015447 dated Feb. 17, 2021.
International Search Report and Written Opinion issued by ISA/US on Jun. 15, 2020 for International Application No. PCT/US2020/015444.
DE102016007669_google_translation.
CN104116484_google_translation.
(Continued)

*Primary Examiner* — Suzette J Gherbi
(74) *Attorney, Agent, or Firm* — James H. Ortega; David W. Carstens; Carstens, Allen & Gourley, LLP

(57) ABSTRACT

A stent apparatus for use in surgical applications having a hollow tubular section with a proximal end and a distal end. The stent apparatus may also have a plurality of radially extending anchoring points centrally located between the proximal and distal ends. The stent being compressible can also include a sheath that is of a material that can be pulled away to remove it from the stent and deploy the stent and the plurality of radially extending anchoring points.

20 Claims, 11 Drawing Sheets

Related U.S. Application Data application No. 16/752,315, filed on Jan. 24, 2020, now Pat. No. 11,666,464.

(60) Provisional application No. 62/797,933, filed on Jan. 28, 2019, provisional application No. 62/797,932, filed on Jan. 28, 2019, provisional application No. 62/797,944, filed on Jan. 28, 2019.

(51) Int. Cl.

| | | |
|---|---|---|
| *A61B 5/026* | (2006.01) | |
| *A61F 2/848* | (2013.01) | |
| *A61F 2/88* | (2006.01) | |
| *A61F 2/95* | (2013.01) | |
| *A61F 2/966* | (2013.01) | |
| *A61B 17/11* | (2006.01) | |

(52) U.S. Cl.
CPC .............. *A61F 2/88* (2013.01); *A61F 2/90* (2013.01); *A61F 2/95* (2013.01); *A61B 2017/1107* (2013.01); *A61B 2017/1132* (2013.01); *A61F 2002/8483* (2013.01); *A61F 2002/8486* (2013.01); *A61F 2210/009* (2013.01); *A61F 2220/0008* (2013.01)

(58) Field of Classification Search
CPC ............. A61F 2002/9665; A61F 2/848; A61B 2017/1107; A61B 2017/1132; A61B 2017/00336; A61B 17/11
See application file for complete search history.

(56) References Cited

U.S. PATENT DOCUMENTS

| | | | |
|---|---|---|---|
| 4,873,965 A | 10/1989 | Danieli | |
| 5,141,516 A | 8/1992 | Detweiler | |
| 5,349,133 A | 9/1994 | Rogers | |
| 5,492,131 A | 2/1996 | Galel | |
| 5,507,725 A | 4/1996 | Savage et al. | |
| 5,536,236 A | 7/1996 | Yab et al. | |
| 5,562,641 A | 10/1996 | Flomenblit et al. | |
| 5,573,493 A | 11/1996 | Sauer et al. | |
| 5,733,325 A | 3/1998 | Robinson et al. | |
| 5,746,766 A * | 5/1998 | Edoga .................. | A61F 2/95 606/198 |
| 5,851,218 A | 12/1998 | Lev | |
| 5,968,091 A * | 10/1999 | Pinchuk ................. | A61F 2/90 427/2.24 |
| 6,083,257 A * | 7/2000 | Taylor ................... | B21F 45/00 623/1.46 |
| 6,270,524 B1 * | 8/2001 | Kim ...................... | A61F 2/89 623/1.11 |
| 6,361,559 B1 | 3/2002 | Houser et al. | |
| 6,485,513 B1 | 11/2002 | Fan | |
| 6,517,574 B1 | 2/2003 | Chuter | |
| 6,565,581 B1 | 5/2003 | Spence et al. | |
| 6,699,263 B2 | 3/2004 | Cope | |
| 6,786,919 B1 * | 9/2004 | Escano ................. | A61F 2/90 623/1.53 |
| 6,899,672 B2 | 5/2005 | Chin et al. | |
| 7,090,637 B2 | 8/2006 | Danitz et al. | |
| 7,476,256 B2 | 1/2009 | Meade et al. | |
| 7,678,068 B2 | 3/2010 | Levine et al. | |
| 7,766,962 B1 | 8/2010 | Quinn | |
| 8,097,009 B2 | 1/2012 | Wu et al. | |
| 8,211,025 B2 | 7/2012 | Donaldson et al. | |
| 8,298,161 B2 | 10/2012 | Vargas | |
| 8,360,968 B2 | 1/2013 | Hadani | |
| 8,444,549 B2 | 5/2013 | Viola et al. | |
| 8,512,232 B2 | 8/2013 | Rothberg et al. | |
| 8,615,288 B2 | 12/2013 | Govari et al. | |
| 8,920,482 B2 | 12/2014 | McHugo | |
| 9,220,568 B2 | 12/2015 | Bromander et al. | |
| 9,326,870 B2 | 5/2016 | Berglund et al. | |
| 9,757,856 B2 | 9/2017 | Oyola et al. | |
| 9,820,746 B2 * | 11/2017 | Imran .................... | A61B 17/11 |
| 9,949,692 B2 | 4/2018 | Hunter | |
| 10,299,950 B2 | 5/2019 | Campbell et al. | |
| 10,420,661 B2 * | 9/2019 | Hodgkinson ........... | A61F 2/915 |
| 10,542,931 B2 * | 1/2020 | Kuraguntla ............ | A61B 5/0215 |
| 11,033,377 B2 | 6/2021 | Houston et al. | |
| 11,039,838 B2 | 6/2021 | Binmoeller et al. | |
| 11,259,945 B2 | 3/2022 | Berra | |
| 11,491,003 B2 | 11/2022 | Arbefeuille et al. | |
| 11,596,408 B2 | 3/2023 | Lukin et al. | |
| 11,696,843 B2 * | 7/2023 | Pung .................... | A61F 2/90 623/1.11 |
| 11,724,009 B2 * | 8/2023 | Paquin ................. | A61L 31/148 424/426 |
| 2001/0004696 A1 | 6/2001 | Roberts et al. | |
| 2002/0029076 A1 | 3/2002 | Yee | |
| 2002/0099405 A1 | 7/2002 | Yurek et al. | |
| 2002/0143347 A1 | 10/2002 | Cole et al. | |
| 2002/0151957 A1 * | 10/2002 | Kerr ..................... | A61F 2/07 623/1.13 |
| 2003/0135266 A1 | 7/2003 | Chew et al. | |
| 2003/0216801 A1 | 11/2003 | Tweden et al. | |
| 2003/0225445 A1 | 12/2003 | Derus et al. | |
| 2004/0082945 A1 * | 4/2004 | Clague ................. | A61B 18/14 606/32 |
| 2004/0116999 A1 | 6/2004 | Ledergerber | |
| 2004/0167604 A1 | 8/2004 | Stinson | |
| 2005/0049480 A1 * | 3/2005 | Gray ..................... | A61L 31/022 600/407 |
| 2005/0154444 A1 | 7/2005 | Quadri | |
| 2005/0154448 A1 | 7/2005 | Cully et al. | |
| 2006/0052736 A1 | 3/2006 | Tweden et al. | |
| 2006/0074478 A1 * | 4/2006 | Feller, III ......... | A61B 17/12118 623/1.11 |
| 2006/0149349 A1 | 7/2006 | Garbe | |
| 2006/0211984 A1 * | 9/2006 | Blank ................... | B29C 61/02 604/102.02 |
| 2007/0055339 A1 | 3/2007 | George et al. | |
| 2007/0067014 A1 | 3/2007 | Ke et al. | |
| 2007/0106373 A1 * | 5/2007 | Houston .............. | F16L 11/121 623/1.32 |
| 2007/0142711 A1 | 6/2007 | Bayer et al. | |
| 2007/0179598 A1 * | 8/2007 | Duerig ................. | A61F 2/064 623/1.44 |
| 2008/0132906 A1 | 6/2008 | Rasmussen | |
| 2008/0255653 A1 | 10/2008 | Schkolnik | |
| 2009/0023998 A1 | 1/2009 | Ratnakar | |
| 2009/0171437 A1 | 7/2009 | Brocker et al. | |
| 2009/0281557 A1 | 11/2009 | Sander et al. | |
| 2009/0287293 A1 | 11/2009 | Mailhot | |
| 2010/0030320 A1 * | 2/2010 | Feller, III .............. | A61F 2/95 623/1.11 |
| 2010/0168835 A1 | 7/2010 | Dorn | |
| 2010/0217082 A1 | 8/2010 | Ito et al. | |
| 2010/0262171 A1 | 10/2010 | Wu et al. | |
| 2011/0190870 A1 | 8/2011 | Hastings et al. | |
| 2011/0264196 A1 * | 10/2011 | Savage ................ | A61F 2/2418 623/2.11 |
| 2012/0071721 A1 | 3/2012 | Remijan et al. | |
| 2012/0123464 A1 | 5/2012 | Rasmussen et al. | |
| 2012/0290072 A1 * | 11/2012 | Theobald ................ | A61F 2/82 623/1.15 |
| 2013/0035751 A1 | 2/2013 | Shalev | |
| 2013/0144380 A1 | 6/2013 | Quadri et al. | |
| 2013/0190741 A1 | 7/2013 | Moll et al. | |
| 2013/0331927 A1 * | 12/2013 | Zheng .................... | A61F 2/90 623/1.19 |
| 2014/0081415 A1 | 3/2014 | Ruberti et al. | |
| 2014/0228936 A1 | 8/2014 | Kassab et al. | |
| 2014/0236064 A1 | 8/2014 | Binmoeller et al. | |
| 2014/0277442 A1 | 9/2014 | Seddon et al. | |
| 2014/0303599 A1 | 10/2014 | Heideman et al. | |
| 2015/0328022 A1 | 11/2015 | Hansen et al. | |
| 2015/0366439 A1 | 12/2015 | Luo et al. | |
| 2016/0120638 A1 | 5/2016 | Michalak | |
| 2016/0242940 A1 * | 8/2016 | Krautkremer ............ | A61F 2/04 |

(56) References Cited

U.S. PATENT DOCUMENTS

| | | |
|---|---|---|
| 2016/0256610 A1* | 9/2016 | Zhou ................... A61L 31/06 |
| 2016/0310077 A1 | 10/2016 | Hunter et al. |
| 2017/0079785 A1 | 3/2017 | Li |
| 2017/0086929 A1 | 3/2017 | Moll et al. |
| 2017/0128072 A1 | 5/2017 | Wang et al. |
| 2017/0296038 A1 | 10/2017 | Gordon et al. |
| 2017/0330665 A1 | 11/2017 | Zareei et al. |
| 2018/0207007 A1 | 7/2018 | Giasolli et al. |
| 2019/0239879 A1 | 8/2019 | Zilla et al. |
| 2020/0094398 A1 | 3/2020 | Young et al. |
| 2020/0170776 A1* | 6/2020 | Folan ................. A61M 27/002 |
| 2020/0237534 A1* | 7/2020 | Manolidis .............. A61B 5/026 |
| 2020/0237540 A1* | 7/2020 | Manolidis ............... A61F 2/848 |
| 2021/0077247 A1 | 3/2021 | Shalev et al. |
| 2021/0205007 A1 | 7/2021 | Anderson et al. |
| 2021/0393424 A1* | 12/2021 | McWeeney ............ A61F 2/966 |
| 2022/0273365 A1 | 9/2022 | Rege et al. |
| 2022/0303150 A1 | 9/2022 | Jensen et al. |
| 2023/0026939 A1 | 1/2023 | Manolidis |
| 2023/0048537 A1 | 2/2023 | Arbefeuille et al. |
| 2023/0132550 A1* | 5/2023 | Vong ...................... A61F 2/844 623/1.11 |
| 2023/0277294 A1* | 9/2023 | Folan ....................... A61F 2/90 623/1.2 |
| 2023/0310186 A1* | 10/2023 | Nagano .................... A61F 2/90 623/1.15 |
| 2023/0355381 A1* | 11/2023 | Peckels ................ A61F 2/2433 |

FOREIGN PATENT DOCUMENTS

| | | | |
|---|---|---|---|
| EP | 2063823 | A2 | 6/2009 |
| GB | 2452480 | A | 11/2009 |
| JP | 2012065933 | A | 4/2012 |
| WO | 9415549 | A1 | 7/1994 |
| WO | 9423669 | A1 | 10/1994 |
| WO | 0045737 | A1 | 8/2000 |
| WO | 02056798 | A2 | 7/2002 |
| WO | 2008025855 | A2 | 3/2008 |
| WO | 2008066917 | A1 | 6/2008 |
| WO | 2009091899 | A2 | 7/2009 |
| WO | WO2011116913 | A1 | 9/2011 |
| WO | 2016069274 | A1 | 5/2016 |
| WO | 2016134148 | A1 | 8/2016 |
| WO | WO18005861 | A1 | 1/2018 |
| WO | 2018068106 | A1 | 4/2018 |

OTHER PUBLICATIONS

International Search Report and Written Opinion issued by ISA/US on Apr. 22, 2020 for International Application No. PCT/US2020/015447.

International Search Report and Written Opinion issued by ISA/US on Apr. 28, 2020 for International Application No. PCT/US2020/015439.

* cited by examiner

STENT AND STENT DELIVERY FOR VASCULAR SURGERY

CROSS-REFERENCE TO RELATED APPLICATION

The present disclosure claims priority to and is a nonprovisional conversion of U.S. Provisional Patent Application No. 62/797,932, filed Jan. 28, 2019, and is a continuation-in-part of U.S. patent application Ser. No. 16/752,315, filed Jan. 24, 2020, which claims priority from U.S. Provisional Patent Application No. 62/797,933, filed Jan. 28, 2019, and is a continuation-in-part of U.S. patent application Ser. No. 16/752,343, filed Jan. 24, 2020, which claims priority from U.S. Provisional Patent Application No. 62/797,944, filed Jan. 28, 2019, all of which is incorporated herein by reference in its entirety for all purposes.

TECHNICAL FIELD

The present invention relates to a stent and the delivery of said stent. More particularly, and not by way of limitation, the present invention is directed to an apparatus, method, or system for a stent and stent delivery.

BACKGROUND

There are many different types of surgeries that can be conducted daily in hospitals across the world. One such surgery is free flap reconstruction. Free flap reconstruction is a well-established method of reconstruction of both soft tissue and bone or composite defects in a wide variety of surgeries. Free flaps are used in order of frequency in head and neck reconstruction, breast reconstruction, orthopedic surgery and a variety of other specialties. Head and neck surgery in particular is a heavy user of free flap reconstruction. This is due to the complexity of defects in a critical area where restoration of functions such as deglutition, phonation, and mastication is of paramount importance in addition to cosmesis.

Free flap reconstruction involves the transfer of tissue from a distant part of the body to the area that needs to be reconstructed. The principle in operation behind this concept is that tissues in the body are supplied in a segmental function. That is that a segment of skin subcutaneous tissue fascia muscle bone, or any combination of these can be harvested according to specific location. The transfer of tissue is completed when the free flap vessels (artery and vein) are joined to the donor vessels and then the flap is set into the defect.

Donor vessels, are selected from appropriate vessels to match the diameter of the recipient vessels (free flap vessels). In the neck, these are usually branches of the external carotid artery and one of the many veins in the head and neck or the jugular vein itself. Each of the donor vessels are dissected from surrounding tissue, and their edges prepared for anastomosis. In free flap reconstruction, vessels are raised in situ and the vascular supply is dissected out carefully and traumatically. The vascular supply is then sectioned, preferably at a length of vessel that is appropriate for an anastomosis without tension. This is not always possible as different free flaps have different lengths of vessels according to where they are harvested. For example, free rectus vascular pedicle may have a max length of 8 cm, while a radial forearm vascular pedicle may have a max length of 15-20 cm.

Once the vessels are extracted from the appropriate location, the edge preparation begins. The vessel preparation process can take approximately one hour and is performed under optimal conditions with an operating microscope and/or magnifying loops. Considerable skill is required that comes with prolonged surgical training. The anastomoses (joining) themselves are approximately 20 minutes per vessel anastomosis. Venous couplers reduce the amount of time required for venous anastomoses. However, these venous couplers still require suturing for each venous anastomoses, taking considerable time and increasing the time a patient is under anesthesia. There are two general types of anastomoses, an end to end and an end to side. An end-to-end anastomoses is preferred because it is performed rapidly without additional problems and because the vascular dynamics are that of linear flow which gives lesser complication rates. End to end anastomoses account for the majority of vessel joining. However, currently these operations and/or couplings still require significant suturing time, that can lead to other complications.

Thus, it would be advantageous to have an apparatus and system for stent and stent delivery for vascular surgery that overcomes the disadvantages of the prior art. The present invention provides such an apparatus and system.

BRIEF SUMMARY

The present disclosure is directed to a stent and delivery of said stent during open surgery. Thus, in one aspect, the present invention is directed to a stent that may self-modify, or self-expand during or upon delivery.

In another aspect, the present disclosure is directed to a stent that may be delivered with an outer sheath or protective layer. In yet another aspect, the present invention is directed to a stent that may be delivered through a syringe or push release mechanism.

Therefore, in one aspect, the present disclosure is directed to a modified self-expanding stent that may be used to perform anastomoses with novel carriers for the endoluminal application of the stent. The stent may have anchor points or atraumatic points.

Thus, in one aspect, the present disclosure is directed to rapidly performing anastomoses without vessel preparation or suturing. In another aspect, the present invention is directed to lengthening the pedicle during grafts and/or distention of the lumen of the vessel during stent operation.

BRIEF DESCRIPTION OF THE DRAWINGS

The novel features believed characteristic of the disclosure are set forth in the appended claims. The disclosure itself, however, as well as a preferred mode of use, further objectives and advantages thereof, will be best understood by reference to the following detailed description of illustrative embodiments when read in conjunction with the accompanying drawings, wherein:

DETAILED DESCRIPTION

An embodiment of the disclosure will now be described. It should be noted that while vascular, and/or microvascular surgeries and/or surgical methods will be described herein, the present disclosure could also be utilized in any number of surgeries, including, but not limited to those for, the head, neck, sinus, nasal, ear, heart, lung, arteries, veins, brain, nerves, organs, vessels, and/or any other human or animal surgery. While the description will be related to operations on human, it would be understood that those in the veterinarian field could also benefit from the present disclosure. Some examples of the disclosure may also benefit the plumbing, electrical, or other related fields.

Descriptions herein will be made with respect to a gravitational reference, but such descriptions should not be considered limiting. As it would be understood, unless otherwise noted a reference to a left, or right of an object could be mirrored or flipped, similarly unless otherwise noted a reference to up or down could be mirrored or flipped. The stents, and/or stent delivery mechanisms disclosed herein can be manufactured, made, and/or formed with any number of materials, including, but not limited to, wood, plastics, silicon, metal, metal alloys, synthetic materials, polymers, absorbable polymers, Teflon, Mylar, carbon fiber, other like materials, or combinations thereof.

Figure 1A:
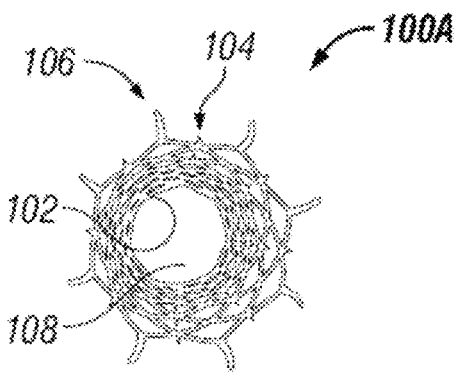
FIG. 1A is an illustration of a coil stent in a front view.

FIG. 1A is an illustration of a coil stent 100A in a front view. The coil stent 100A and/or stent body 102 may in at least one version, be made or manufactured with an expandable or modifiable material such as, but not limited to, elastic polymers, elastic alloys, metals, plastics, synthetic materials, and/or combinations thereof. In some versions, the stent body 102 is a hollow cylinder or hollow tubular body that may have an inner diameter and corresponding inner circumference, and an outer diameter and corresponding outer circumference.

Along an outer circumference of the stent body 102, there may be a stent body anchor 104. There may also be one or more stent body anchor(s), such that there is at least one body anchor 104 along the outer circumference of the stent body 102. The stent body anchor 104 may be, but is not limited to, an anchor, a spike, a barb, an atraumatic anchor, a prong, a point, a pin, and/or any combination thereof. In at least one embodiment, an atraumatic anchor can assist in securing a vessel to the stent. The stent body anchor 104 may be utilized to secure a donor vessel and/or a recipient vessel to the coil stent 100A. The stent body 102 may also have at least one stent end anchor 106. The stent end anchor 106 may be, but are not limited to, spike(s), barb(s), atraumatic anchor(s), prong(s), point(s), pin(s), and/or any combination(s) thereof.

An aperture 108 can be formed by the stent body 102. The aperture may be defined by the stent body 102, and more particularly by the inner diameter, and/or inner circumference of the stent body 102. It would be understood that the aperture 108 can have many cross-sections and/or profiles, such as but not limited to, a circle, an oval, a square, a rectangle, a polygon, a cone, a pyramid, other shapes or profiles, and/or combinations thereof.

Figure 1B:
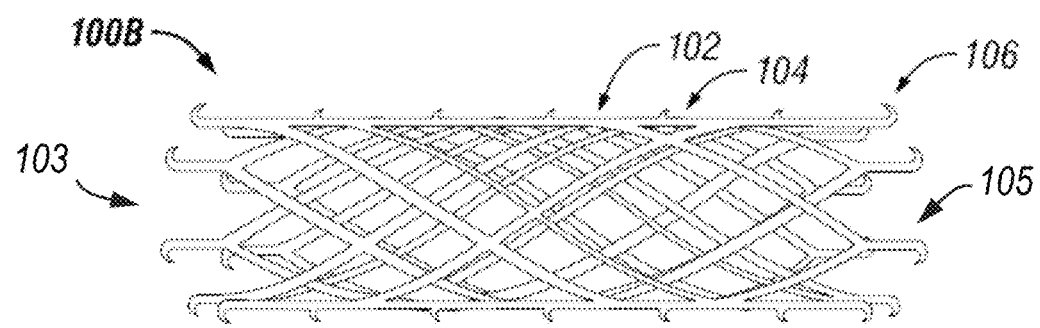
FIG. 1B is an illustration of a coil stent in a side view.

FIG. 1B is an illustration of a coil stent 100B in a side view. A stent body 102 can be comprised of many different shapes, cross-sections, and/or profiles. In one example, the stent body 102 may have a top, and a bottom that can be in planes parallel to each other, and a first end 103, and a second end 105, the second end 105 is distal from the first end 103. In alternative examples, the top and bottom of the stent body 102 may not be in parallel planes. For example, a vessel (not illustrated) may have a narrowed or narrowing section that requires the stent body 102 to be smaller at one end, and larger at the other end. Creating a situation where the top would be in a plane that converges with a plane parallel to the bottom of the stent body 102.

The stent body 102 may have at least one anchor along the outer circumference, and/or ends of the stent body 102. The stent body anchor 104, or at least one stent body anchor, may be placed in a centrally located and/or various locations along the outer circumference of the stent body 102. The anchors may be atraumatic or non-puncturing, or a form of puncturing or traumatic anchor. For example, in a low pressure or slow blood flow vessel atraumatic anchors may be used to avoid damage to the vessels with low blood flow through them. In another example, the coil stent 100B may also be utilized in a high pressure or fast blood flow vessel utilizing the anchors 104/106 to secure the coil stent 100B in place through the use of a puncturing anchor and/or a combination of puncturing and atraumatic anchors.

During surgeries that allow for end-to-end anastomoses the donor vessel (not illustrated) and the recipient vessel (not illustrated) can be affixed to the coil stent 100B via the stent body anchor(s) 104 and/or the stent end anchor(s) 106. The vessels do not have to be prepared in a traditional manner because the anchor(s) 104/106 allow for the securing of the donor vessel and/or the recipient vessel with no need for suturing of the vessels. There is also a decrease in the amount of time required preparing the ends of the vessels. The stent body anchor(s) 104 can be manufactured with a length sufficient to puncture through the lumen or wall of both the donor vessel and the recipient vessel. The stent end anchor(s) 106 can be manufactured with a length sufficient to puncture through the lumen or wall of the donor vessel or the recipient vessel.

Figure 2A:
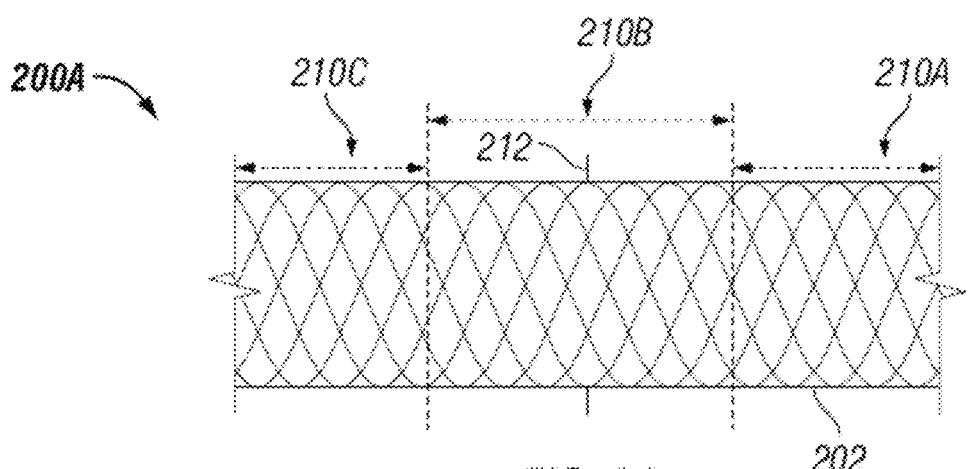
FIG. 2A is an illustration of a stent in a side view.

FIG. 2A is an illustration of a stent 200A in a side view. A stent body 202 of the stent 200A can be comprised of multiple sections, such as but not limited to a first stent body section 210A, a second stent body section 210B, and/or a third stent body section 210C. These stent body sections may be constructed, formed, or manufactured of plastics, silicon, metal, metal alloys, synthetic materials, polymers, absorbable polymers, Teflon, Mylar, carbon fiber, other like materials, or combinations thereof. Additionally, in at least one version, each of the stent body section may be constructed of a different material. The different materials can allow for different expansion or deformation rates for each stent body section for an expandable or modifiable stent. The stent body sections can also be a first stent end section (proximal section), a central stent section (attachment section), and a second stent end section (distal section). It would be understood that the proximal and distal sections may also be reversed in some examples. Each of the end sections may also have their own proximal, attachment, and/or distal sections.

Radial anchor(s) 212 or radial anchor point can be placed radially along the stent body 202. In one example, the radial anchor(s) 212 may be placed centrally between each end of the stent body 202 within the second stent body section 210B or the central stent section. In another example, the radial anchor(s) 212 may be comprised of more than one radial anchor, or at least one radial anchor, and/or placed along the first stent body 210A, second stent body 210B, and third stent body 210C.

Figure 2B:
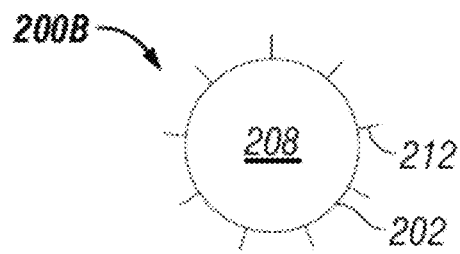
FIG. 2B is an illustration of a stent in a front view.

FIG. 2B is an illustration of a stent 200B in a front view. The stent body 202 may comprise an aperture 208. The aperture 208 alone or in combination with the stent body 202 may define a lumen of stent 200B. The aperture 208 and/or the lumen of the stent may also vary with the expandability and modifications of the stent 200B. The materials of formation, construction, or manufacture for the stent 200B may have specific forces on them for expansion and/or modification such that in one example the stent 200B may expand from a first diameter to a second diameter that is approximately double or two times the first diameter. It would be understood that the expansion rate could range from 1 to 100 times the original size of the stent or other expandable section.

The aperture 208 and/or stent body 202 may have radial anchor(s) 212 along the outer or inner circumference of stent body 202. In at least one example, the radial anchor(s) 212 may be spaced with equal distance between them. In alternative examples, the radial anchor(s) 212 may be unequally spaced along the circumference of stent body 202. The expandability and modifiability of the stent 200B can allow the radial anchor(s) 212 to securing a donor and/or recipient vessel.

Figure 3A:
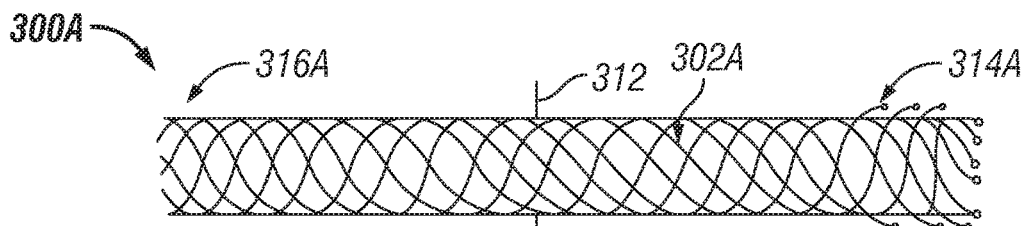
FIG. 3A is an illustration of a compressed expandable stent in a side view.

FIG. 3A is an illustration of a compressed expandable stent 300A in a side view. The compressed expandable stent 300A can have an unexpanded stent body 302A, with the unexpanded stent body 302A having at least one radial anchor 312. The compression of the uncompressed expandable stent 300A can be generated by the materials utilized to form, construct, and/or manufacture the stent. The materials can have an elasticity, or tensile strength based on the modular, sectional, and/or geometrical structure chosen for the specific stent. The unexpanded stent body 302A may also have atraumatic anchor(s) 314A, and/or traumatic anchor(s) 316A that may be in a compressed state. Traumatic anchor(s) would reference an anchor that can puncture or be invasive to the wall or lumen of a vessel but this would be an acceptable level of injury and/or be minimally invasive to secure the stent in place within a donor and/or recipient vessel. The atraumatic anchor(s) 314A and/or traumatic anchor(s) 316A may be in a compressed or unexpanded state prior to and during initial delivery or installation of the stent. A device can be utilized to deliver the stent to a donor and/or recipient vessel and initiate a decompression, expansion, and/or modification of the stent properties, the unexpanded stent body 302A, and/or anchor(s) 314A/316A.

Figure 3B:
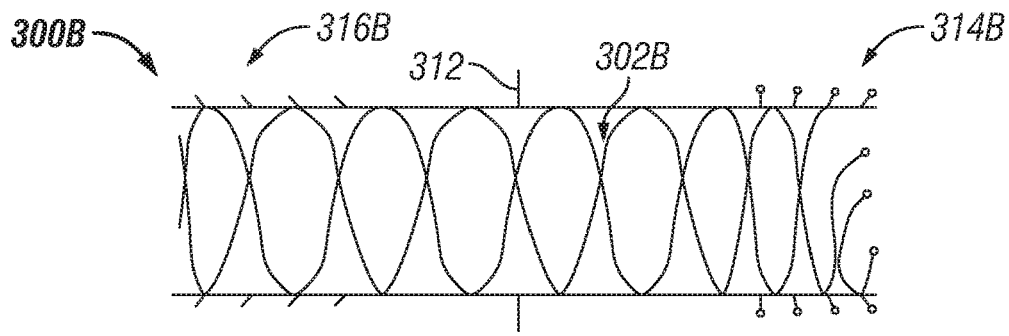
FIG. 3B is an illustration of an uncompressed expandable stent in a side view.

FIG. 3B is an illustration of an uncompressed expandable stent 300B in a side view. The uncompressed expandable stent 300B can have an expanded stent body 302B. The expanded stent body 302B can have at least one radial anchor(s) 312 coupled along the circumference of the stent body 302. The compression of the uncompressed expandable stent 300A can be generated by the materials utilized to form, construct, and/or manufacture the stent. The materials can have an elasticity, or tensile strength based on the modular, sectional, and/or geometrical structure chosen for the specific stent.

The at least one radial anchor(s) 312 can be utilized to secure a donor vessel and/or a recipient vessel (not illustrated). The expanded stent body 302B may also have atraumatic anchor(s) 314B, and/or traumatic anchor(s) 316B that may be in uncompressed state(s). In a compressed state or first orientation, like that illustrated in FIG. 3A, the anchor(s) can be flat or collapsed against the stent body, and/or unextended from a protected section or area of the stent body. In an uncompressed state or second orientation, the anchor(s) can be released to a designed structure, placement, and/or position based on the self-expanding and/or self-modifying structure of the stent. When in the uncompressed state the anchor(s) 314B/316B may secure against the lumen or wall of the donor and/or recipient vessel. The radial anchor(s) 312 in one example may be compressible, while in alternative examples the radial anchor(s) 312 may be in a fixed position.

Figure 4A:
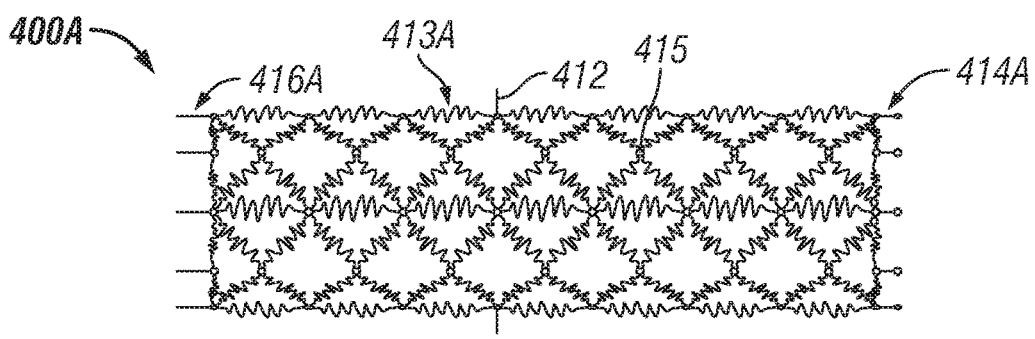
FIG. 4A is an illustration of a compressed expandable stent in a side view.

FIG. 4A is an illustration of a compressed expandable stent 400A in a side view. A compressed stent body 402A may include radial anchor(s) 412, compressed expandable structure 413A, compressed atraumatic anchor(s) 414A, structure node 415, and/or compressed traumatic anchor(s) 416A. The compressed stent body 402A can be in a compressed state because of a compressing structure surrounding and/or containing the compressed stent body 402A in a compressed state, and/or a property of the material utilized to form, construct, and/or manufacture the compressed expandable stent 400A. Radial anchor(s) 412 can in one example be in a fixed position, which radiates outward from the compressed stent body 402A, and/or the outer circumference of the compressed stent body 402A. In an alternative example, the radial anchor(s) 412 may be collapsible and change to a fixed position upon expansion or when the compressed stent body 402A is decompressed.

The compressed expandable structure 413A may be manufactured of a material, such as plastics, silicon, metal, metal alloys, synthetic materials, polymers, absorbable polymers, Teflon, Mylar, carbon fiber, other like materials, or combinations thereof. The material should have a compressibility that allows for the compressed expandable structure 413A to be approximately one-half its normal size, be approximately one-quarter of its normal size, or any other fraction of one whole portion of the expandable structure 413A. The compressed expandable structure 413A may also be formed, constructed, and/or manufactured utilizing a material that may have a memory effect or expansion memory such as a pliable plastic or silicon material, but other materials such as plastics, silicon, metal, metal alloys, synthetic materials, polymers, absorbable polymers, Teflon, Mylar, carbon fiber, other like materials, or combinations thereof, may also be utilized. A memory effect or expansion memory can be described as a material that can be manipulated from a first position to a second position and then return to the first position upon release from the second position.

Figure 4B:
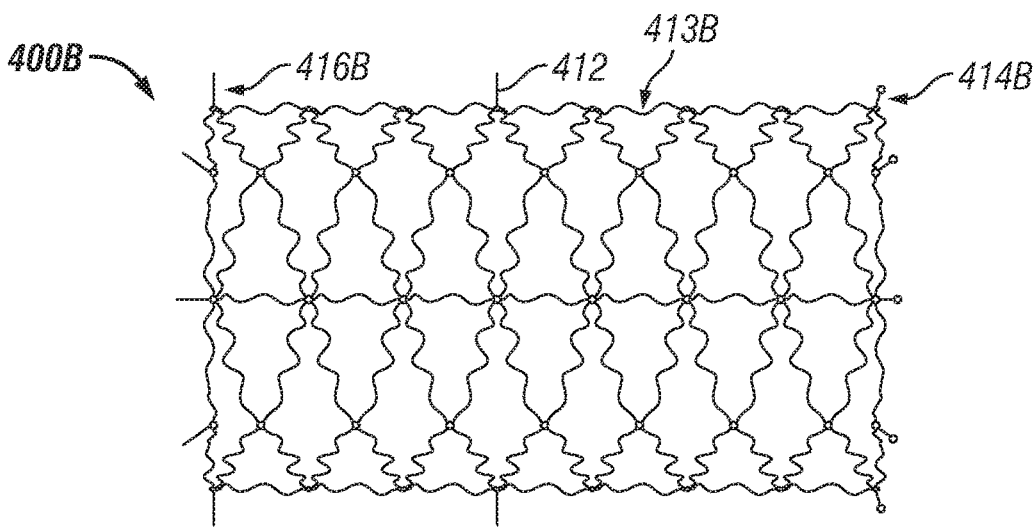
FIG. 4B is an illustration of an uncompressed expandable stent in a side view.

The structure node 415 can provide a connection point for the expandable structure 413A. In at least one example the structure node 415 may be utilized with the expandable structure 413 to create a mesh of nodes. The structure node 415 may be constructed, formed, or manufactured utilizing a material such as, but not limited to, plastics, silicon, metal, metal alloys, synthetic materials, polymers, absorbable polymers, Teflon, Mylar, carbon fiber, other like materials, or combinations thereof. In at least one example, the structure node 415 can be constructed, formed, and/or manufactured with the expandable structure 413A. In alternative examples, the structure node 415 may be connected to, or affixed to the expandable structure 413A through an adhesive, fastener, glue, connector, cement, epoxy, binder, FIG. 4B is an illustration of an uncompressed expandable stent 400B in a side view. An uncompressed stent body 402B may include radial anchor(s) 412, uncompressed expandable structure 413B, uncompressed atraumatic anchor(s) 414B, structure node 415, and/or uncompressed traumatic anchor(s) 416B. For example, a compressed stent body, radial anchor(s), compressed expandable structure, compressed atraumatic anchor(s), structure node, and/or compressed traumatic anchors may be uncompressed and/or expanded by an external or internal force.

When the compressed stent body is uncompressed or expanded, the anchors along the stent body may uncompress or expand radially from the stent body to secure the stent to a donor or recipient vessel. In alternative versions, the anchors may extend linearly or outwardly. The radial anchor(s) 412 may in one example, be in a fixed position that does not allow for compression or expansion. Alternatively, the radial anchor(s) 412 can be compressed along the stent body. In at least one version, the uncompressed atraumatic anchor(s) 414B, and/or uncompressed traumatic anchor(s) 416B may expanded outwardly and/or radially from an axis that runs longitudinally through the uncompressed stent body 402B.

In at least one example, the expansion and/or decompression of the stent body and/or anchor(s) can occur in response to blood flowing through the interior of the stent body. In alternative examples, the expansion and/or decompression of the stent body and/or or anchor(s) can occur in response to an internal or external force, such as but not limited to, a deployment or delivery device, a syringe, a surgical instrument or tool, an electro-mechanical force, an electrical signal, an electromagnetic force, or a magnetic force.

Figure 5A:
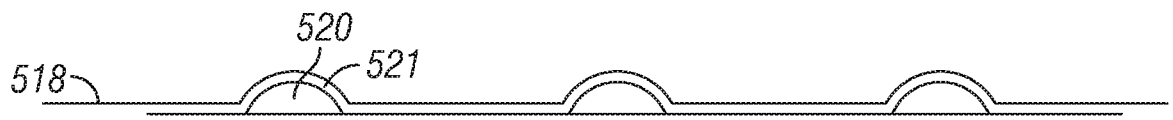
FIG. 5A is an illustration of an atraumatic node.

FIG. 5A is an illustration of an atraumatic node 520. A vessel endolumen 518 can be connected, coupled, and/or secured by an atraumatic node 520. The atraumatic node 520 may have an outer surface 521 that can be smooth or textured. The atraumatic node 520 can also be an atraumatic anchor in alternative versions.

Figure 5B:
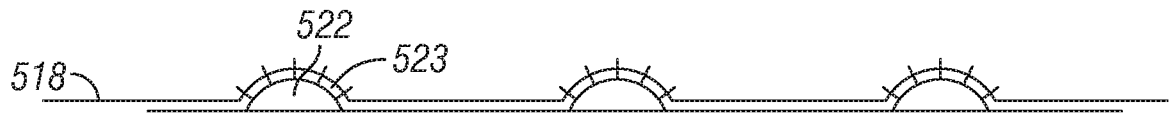
FIG. 5B is an illustration of a barbed node.

FIG. 5B is an illustration of a traumatic node 522. A vessel endolumen 518 can be connected, coupled, and/or secured by a traumatic node 522. The traumatic node 522, may have an outer surface 523 that can be textured, and/or covered with spikes, barbs, points, pins, or other sharp objects that may be affixed or fastened to the traumatic node 522. The fastening can occur through fasteners, such as bolts, nails, screws, tongue and groove, dovetail, slot and pole, or other connection methods. Additionally, adhesives such as, but not limited to, glue adhesives, bonding agents, and other materials that can allow for an adhesive bonding to occur. A combination of fasteners and adhesives can also be utilized. The traumatic node 522 may also be a traumatic anchor in alternative versions.

Figure 6:
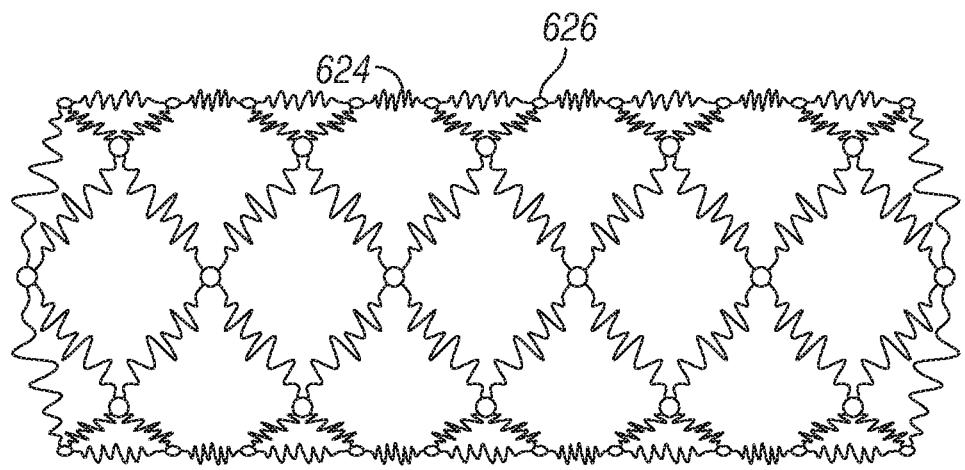
FIG. 6 is an illustration of an expandable stent structure.

FIG. 6 is an illustration of an expandable stent structure. The expandable structure may include an expandable member or structure element 624, and/or an expandable connection node 626. In at least one example, the expandable member 624 and/or expandable connection node 626 can be manufactured with magnetic, and/or shape memory properties. In at least one example, the connection node 626 may interact with other connection nodes to cause a transformation or modification of expandable or structural member 624.

Figure 7A:
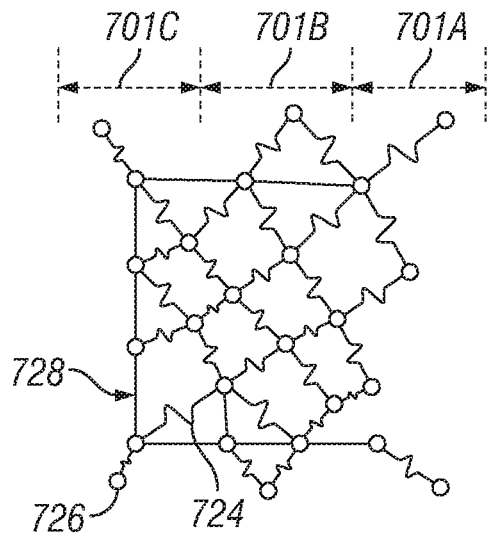
FIG. 7A is an illustration of an expandable stent structure in a side view.

FIG. 7A is an illustration of an expandable stent structure in a side view. An expandable stent may have an expandable structure element 724. A connection node 726 may connect and/or couple expandable structure element 724, with non-expandable structure element 728. The expandable structure element 724, can be formed, constructed, and/or manufactured utilizing materials, such as, but not limited to, plastics, silicon, metal, metal alloys, synthetic materials, polymers, absorbable polymers, Teflon, Mylar, carbon fiber, other like materials, or combinations thereof. Additionally, the expandable structure element 724, in one example, may also have a memory effect that can allow the expandable structure element 724 to compressed or stretched from a first position to a second position, and then upon release from the second position to return to the first position.

A connection node 726 may be formed, constructed, and/or manufactured utilizing materials, such as, but not limited to plastics, silicon, metal, metal alloys, synthetic materials, polymers, absorbable polymers, Teflon, Mylar, carbon fiber, other like materials, or combinations thereof. In at least one example, the connection node 726 may be formed, constructed, and/or manufactured of a same or like materials as the expandable structure element 724. In alternative examples, the connection node 726 can be formed, constructed, and/or manufactured of a different material than the expandable structure element 724. The non-expandable structure element 728 may be formed, constructed, and/or manufactured utilizing materials, such as, but not limited to plastics, silicon, metal, metal alloys, synthetic materials, polymers, absorbable polymers, Teflon, Mylar, carbon fiber, other like materials, or combinations thereof. In at least one example, FIG. 7A may also illustrate a section of a stent apparatus or a first or second end of a stent apparatus, having a proximal end section 701A, an attachment end section 701B, and a distal end section 701C that can couple to a hollow tubular section or structure of the stent apparatus. An expansion may include a linear expansion 730 or radial expansion 732 as shown in FIG. 7B.

Figure 7B:
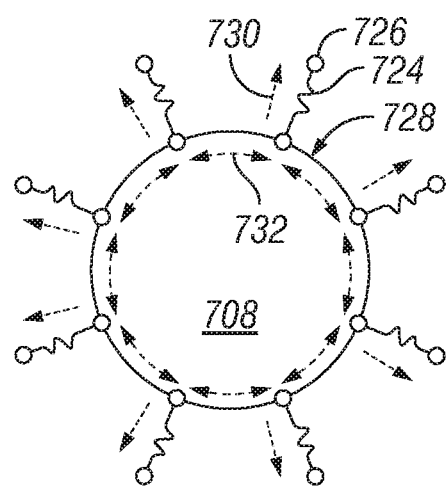
FIG. 7B is an illustration of an expandable stent structure in a front view.

FIG. 7B is an illustration of an expandable stent structure in a front view. An aperture 708 can be defined by the expandable stent structure, and allow for the flow of fluids through the expandable stent structure. The expandable stent structure may be comprised of expandable structure element 724, connection node 726, and/or non-expandable structure element 728. The expandable structure element 724, can allow the expandable stent structure to expand based on conditions. For example, a cover or sheath can be utilized to secure the expandable stent structure in a collapsed, unexpanded, or unmodified state prior to insertion, or use within a patient. The cover or sheath can then be removed to allow the expandable stent structure to expand or self-modify to an expanded or modified state.

Figure 8A:
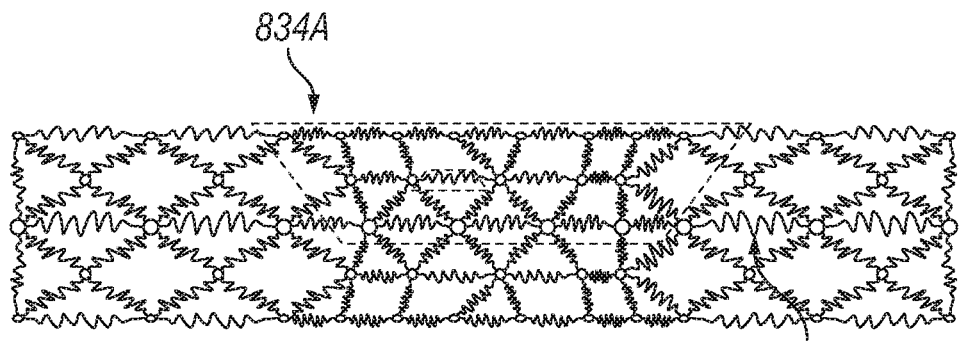
FIG. 8A is an illustration of a modifiable stent in an unmodified state.
Figure 8B:
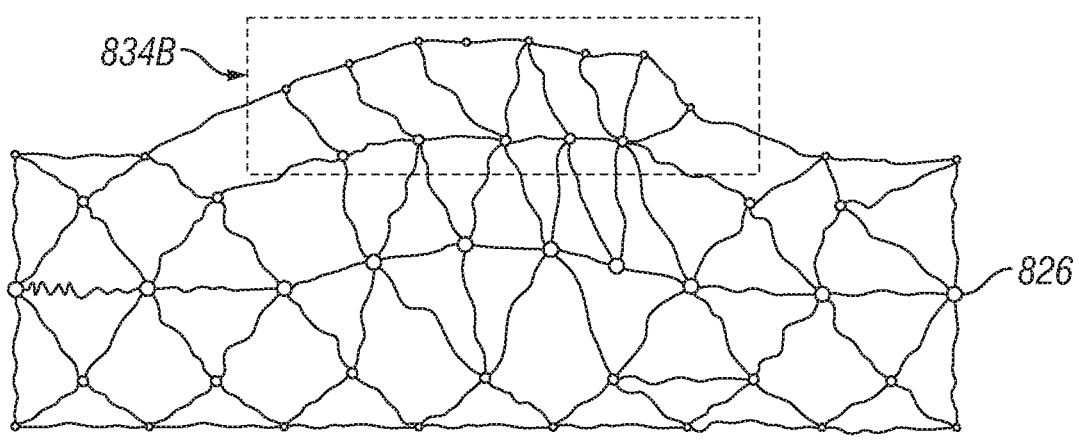
FIG. 8B is an illustration of a modifiable stent in a modified state.

FIG. 8A is an illustration of a modifiable stent in an unmodified state 834A. FIG. 8B is an illustration of a modifiable stent in a modified state 834B. With reference to FIGS. 8A and 8B, a modifiable stent may be modified utilizing expandable stent element(s) 824, and connection node(s) 826. For example, prior to utilization in a patient the stent may be in an unmodified state 834A that allows a modifiable stent to be placed in a patient with relative ease, and allow for the modifiable stent to be sized to fit any number of vessels. A cover or sheath that encloses the modifiable stent can maintain the unmodified state 834A, or the properties of the stent elements may be modified to create a memory effect. The stent elements may also be interconnected elements or interconnecting elements. These properties can include, but are not limited to, the chemical structure, magnetic structure, and/or electrical conductivity structure of stent elements. These properties can be modified, to change the geometry of the modifiable stent to a modified state 834B. For example, the transition from an unmodified state 834A to a modified state 834B, can allow for an expansion of the modifiable stent to secure it to the lumen or wall of a vessel, or set of vessels.

Figure 8C:
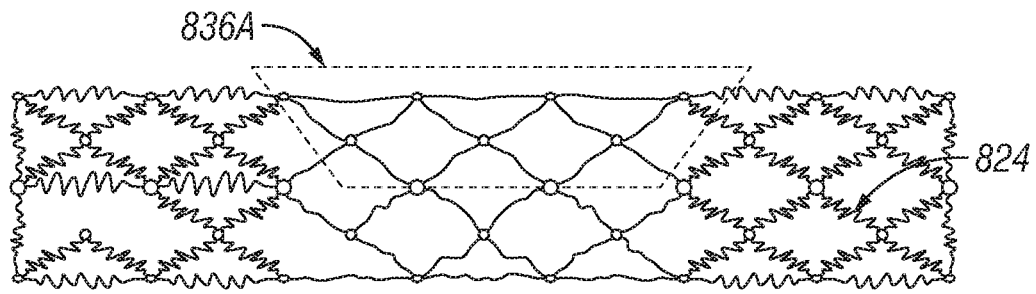
FIG. 8C is an illustration of a modifiable stent in an unmodified state.
Figure 8D:
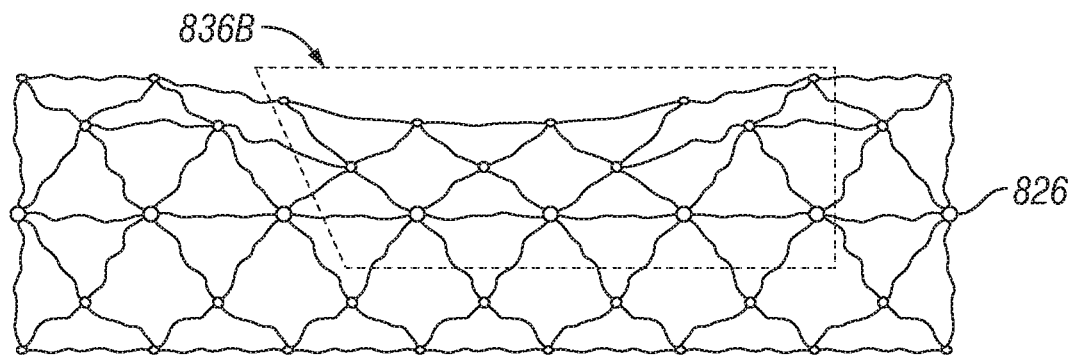
FIG. 8D is an illustration of a modifiable stent in a modified state.

FIG. 8C is an illustration of a modifiable stent in an unmodified state 836A. FIG. 8D is an illustration of a modifiable stent in a modified state 836B. With reference to FIGS. 8C and 8D, a modifiable stent may be modified utilizing expandable stent element(s) 824, and connection node(s) 826. For example, prior to utilization in a patient the stent may be in an unmodified state 836A that allows a modifiable stent to be placed in a patient with relative ease, and allow for the modifiable stent to be sized to fit any number of vessels. The unmodified state 836A can be maintained by an insert or sheath that encompasses the modifiable stent, or the properties of the stent elements may be modified to create a memory effect. These properties can include, but are not limited to, the chemical structure, magnetic structure, and/or electrical conductivity structure of stent elements. These properties can be modified, to change the geometry of the modifiable stent to a modified state 836B. For example, the transition from an unmodified state 836A to a modified state 836B, can allow for a deformation of the modifiable stent to secure it to the lumen or wall of a vessel, or set of vessels.

Figure 9A:
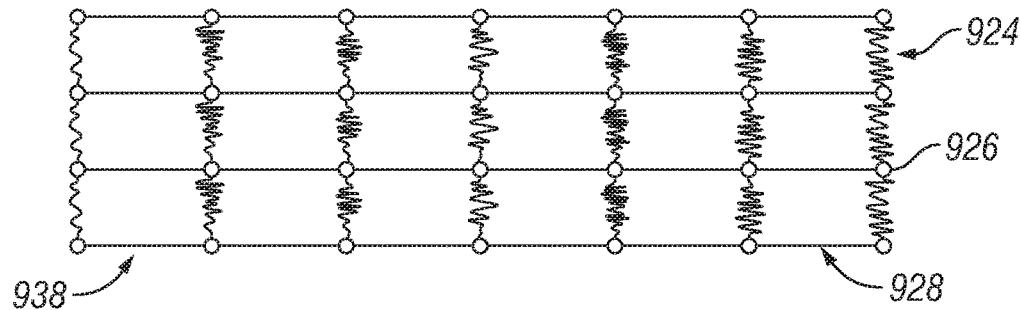
FIG. 9A is an illustration of an expandable stent in an unexpanded state.

FIG. 9A is an illustration of an expandable stent in an unexpanded state 938. The expandable stent can be comprised of expandable structure elements 924, connection node(s) 926, and/or non-expandable structure elements 928. The expandable structure elements 924 can be expanded by outside forces, or based on internal structural forces, for example, if constructed from shape memory alloys. In at least one example, the expandable structure elements 924 would be contained by a sheath, cover, or transportation device (not illustrated) that would maintain the expandable structure elements 924 in a non-expanded or collapsed state, until the sheath, cover, or transportation device is removed. In at least one version, the expandable structure elements 924 can be utilized to create the circumference of the expandable stent (or expandable rings 925 along the length of the expandable stent), and the non-expandable structure 928 elements may be utilized to connect the expandable rings longitudinally via connection node(s) 926.

Figure 9B:
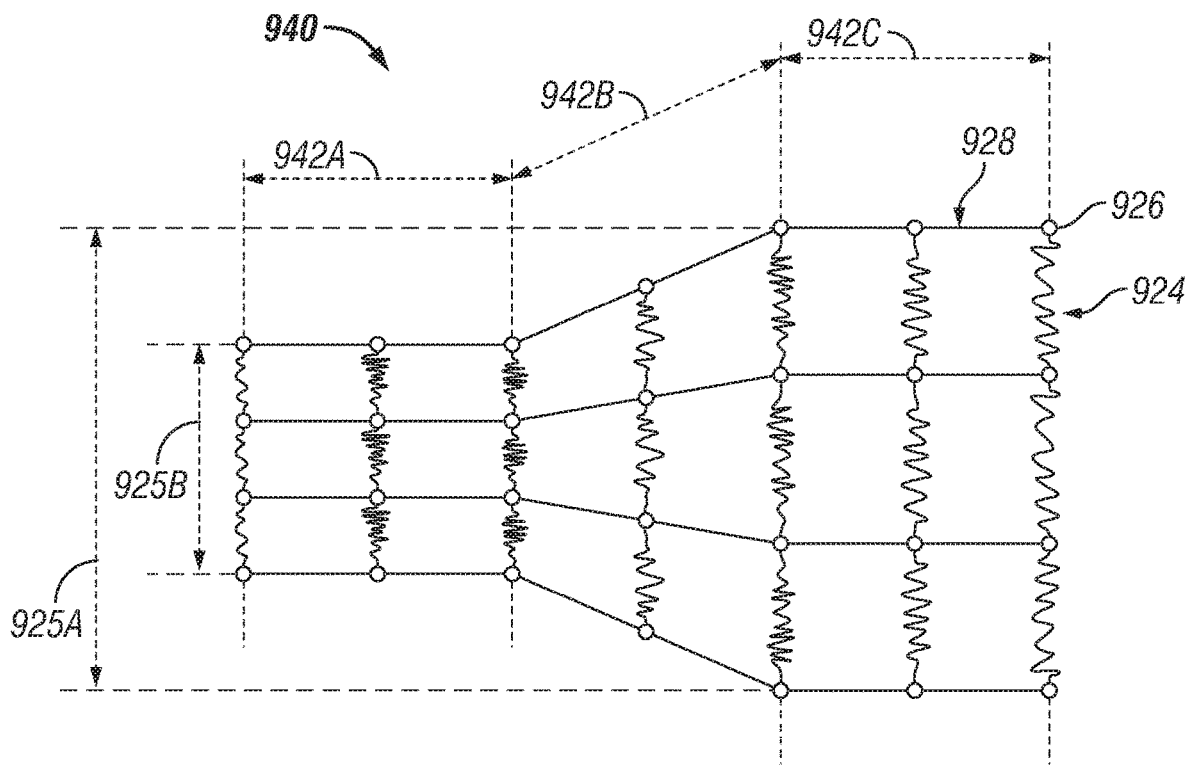
FIG. 9B is an illustration of an expandable stent in a partially expanded state.

FIG. 9B is an illustration of an expandable stent in a partially expanded state 940. The expandable stent is comprised of expandable structure element(s) 924, connection node(s) 926, and/or non-expandable structure element(s) 928. The expandable structure element(s) 924 can be manufactured and/or formed with shape memory alloys, or other materials that allow for an elastic and/or expandable structure. The connection node(s) 926 can be manufactured and/or formed with shape memory alloys, or other materials that allow for an elastic and/or expandable structure, or materials such as, but not limited to, plastic, silicon, metal, synthetic materials, and/or other materials approved for use within a human, or animal body. The non-expandable structure element 928 can be manufactured and/or formed with materials such as, but not limited to, plastic, silicon, metal, synthetic materials, and/or other materials approved for use within a human, or animal body.

The expandable stent can be expanded and/or modified when a sheath, cover, and/or transport device (not illustrated) is removed allowing the expandable structure element(s) 924 to expand to their full potential. For example, an unexpanded portion 942A could be contained within a sheath, cover, and/or transport device (not illustrated) that keeps the expandable structure element(s) 924 in an unexpanded or collapsed state. In another example, a partially expanded portion 942B can be in between the unexpanded state 942A, and a fully expanded state 942C. This partially expanded portion 942B could be the portion of the expandable stent that had recently had a sheath, cover, and/or transport device (not illustrated) recently removed. After a sheath, cover, and/or transport device (not illustrated) is removed, the expandable structure element(s) 924 begin to expand or decompress to an expanded or uncompressed state 942C. In one example, the expandable structure element(s) 924 may return to an original shape or state based on the memory of the material utilized to manufacture the expandable structure element(s) 924. Another example, illustrates when an expanded portion 942A allows for the full expansion or decompression of the expandable structure element(s) 924.

Figure 10A:
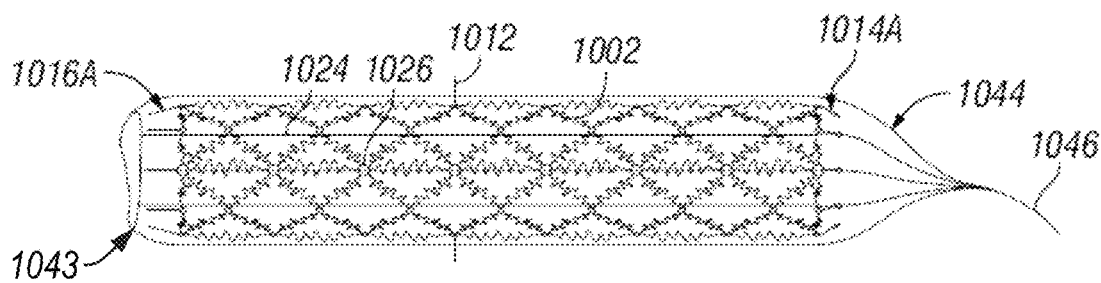
FIG. 10A is an illustration of a barbed expandable stent with a sheath.

FIG. 10A is an illustration of a barbed expandable stent 1000 with a sheath 1043. The sheath 1043 covers and/or contains the barbed expandable stent 1000 and/or stent body 1002 in an unexpanded or collapsed state. The sheath 1043 can assist in covering and/or containing the, atraumatic anchor(s) 1014A and/or traumatic anchor(s) 1016A that are coupled to the stent body 1002. The anchor(s) 1014A and/or 1016A can be utilized on one or more ends of the barbed expandable stent 1000. In at least one example, the anchor(s) 1014A and/or 1016A can be unexpanded or collapsed state, but then after the anchor(s) 1014A and/or 1016A are allowed to expand or transition the anchor(s) 1014A and/or 1016A can interact with vessels or other portions of a human body. The anchor(s) 1014A and/or 1016A may be connected to the stent body 1002 through an expandable structure element 1024, and/or a connection node 1026. In at least one version, the stent body 1002 includes expandable structure element(s) 1024, and connection node(s) 1026. The stent body 1002 can also include radial anchor(s) 1012 that extend radially outward from the stent body 1002. In at least one version, the radial anchor(s) 1012 can be collapsible and/or contained within a sheath, cover, or transport device 1043. In other versions, the radial anchor(s) 1012 are fixed at a specific angle relative to the stent body 1002, the specific angle could range from 15 degrees relative to the stent body 1002, to 165 degrees relative to the stent body 1002. The sheath, cover, or transport device 1043 may also include at least one perforation 1044, and/or a needle 1046. The at least one perforation 1044 allows the sheath, cover, or transport device 1043 to separate around the anchor(s) 1014A, 1016A, and/or 1012. The needle 1046 can allow the sheath, cover, or transport device 1043 to be removed through a vessel lumen or other tissues.

Figure 10B:
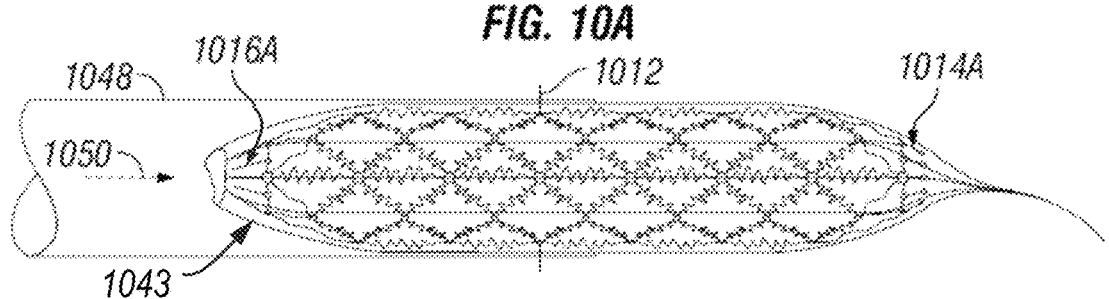
FIG. 10B is an illustration of a barbed expandable stent attached to a donor vessel.

FIG. 10B is an illustration of a barbed expandable stent 1000 attached to a donor vessel 1048. In at least one example, when the barbed expandable stent 1000 is attached to a donor vessel 1048 via the radial anchor(s) 1012. The radial anchor(s) 1012 can be in an uncompressed state, or in a fixed position allowing the anchors to puncture the tissue to be secured to the barbed expandable stent 1000 and/or stent body 1002. Blood flow 1050 through the barbed expandable stent 1012 and/or stent body 1002 can invigorate the healing process of the donor vessel 1048 or recipient vessel.

Figure 10C:
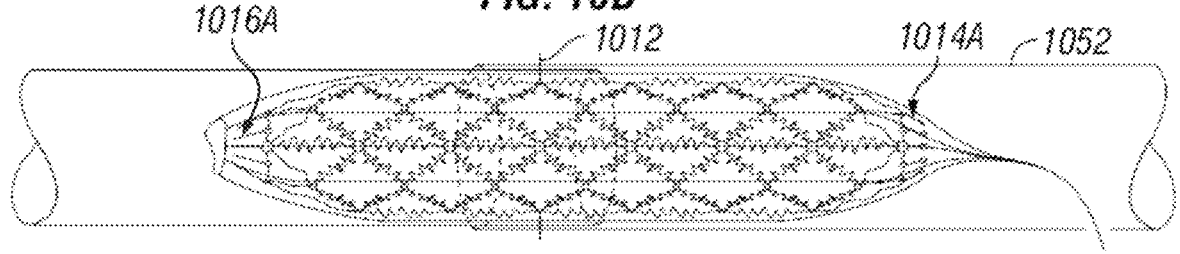
FIG. 10C is an illustration of a barbed expandable stent attached to a donor vessel and a recipient vessel.

FIG. 10C is an illustration of a barbed expandable stent 1000 attached to a donor vessel 1048 and a recipient vessel 1052. The donor vessel 1048 and the recipient vessel 1052 can in at least one example overlap. The overlap can occur in the proximity of the radial anchor(s) 1012. In at least one example, donor vessel 1048 receives the barbed expandable stent 1000 and/or the stent body 1002 within the inner diameter of the of the donor vessel 1048 with the lumens of the vessel being placed over the radial anchor(s) 1012. In other examples, the donor vessel 1048 is placed over the radial anchor(s) 1012, which puncture the vessel lumen or wall, and allow the recipient vessel 1052 to also be placed over the radial anchor(s) 1012. In at least one version, the donor vessel 1048, and/or the recipient vessel 1052 are placed over the sheath 1043 that covers the stent body 1002.

Figure 10D:
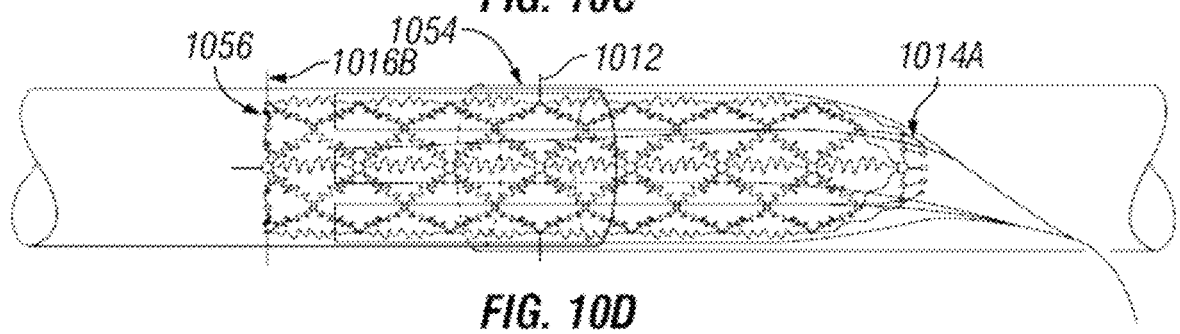
FIG. 10D is an illustration of a barbed expandable stent attached to a donor vessel and a recipient vessel in a partially expanded state.

FIG. 10D is an illustration of a barbed expandable stent 1000 attached to a donor vessel 1048 and a recipient vessel 1052 in a partially expanded state. In at least one example, the anchor(s) 1016B are expanded 1056 in the partially expanded state, allowing them to secure the barbed expandable stent 1000 and/or stent body 1002 to a donor vessel 1048. The radial anchor(s) 1054 may also expand 1054 to couple the barbed expandable stent 1000 and/or the stent body 1002 to the donor vessel 1048 and/or the recipient vessel 1052. The anchor(s) 1014A would remain in a collapsed or unexpanded state until the sheath, cover, and/or transport device 1043 is fully removed.

Figure 10E:
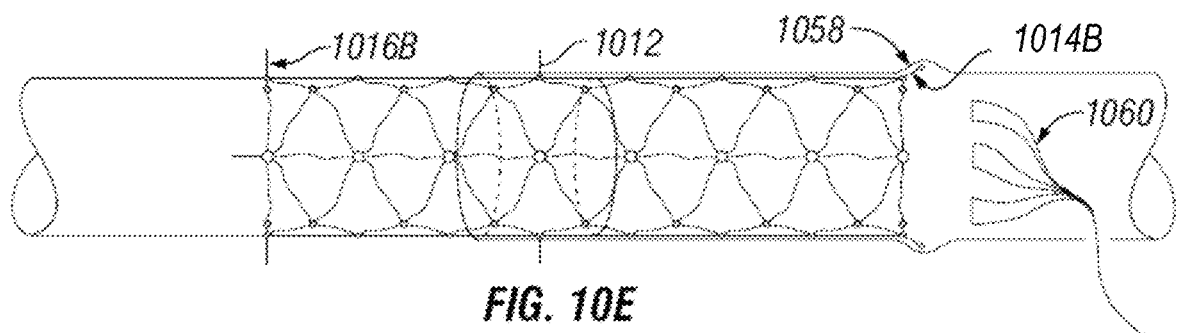
FIG. 10E is an illustration of a barbed expandable stent attached to a donor vessel and a recipient vessel in an expanded state with the sheath removed.

FIG. 10E is an illustration of a barbed expandable stent 1000 attached to a donor vessel 1048 and a recipient vessel 1052 in an expanded state with the sheath 1043 removed. When the sheath, cover, or transport device 1043 is removed from the barbed expandable stent 1000, it can separate into section(s) 1060 along perforations precut or pre-designed into the sheath, or cover material 1043. The expanded state allows the anchor(s) 1014B/1016B to interface, and/or interconnect with the respective vessel or tissue. The anchor(s) 1014B/1016B when expanded 1058 can allow the barbed expandable stent 1000 and/or stent body 1002 to the coupled and/or secured to a vessel or other tissue.

Figure 11A:
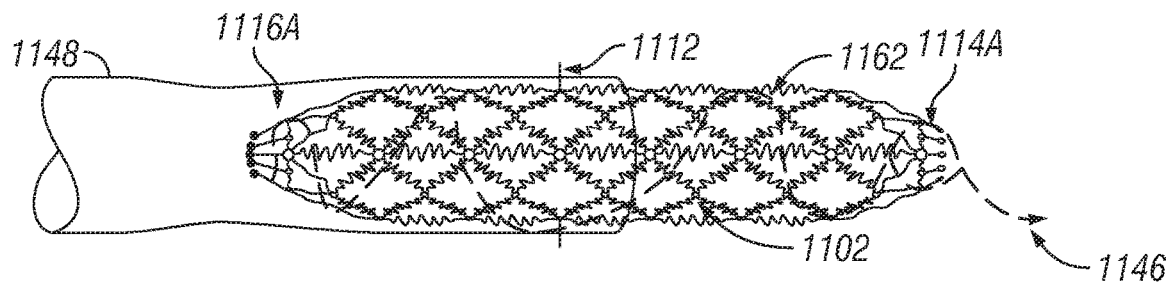
FIG. 11A is an illustration of a barbed expandable stent with donor and recipient vessel anchor(s) in an unexpanded state.

FIG. 11A is an illustration of a barbed expandable stent 1100 with donor and recipient vessel anchor(s) 1114A/1116B in an unexpanded state. The radial anchor(s) 1112 allow for a donor vessel 1148 and/or recipient vessel to be coupled to the barbed expandable stent 1100 and/or the stent body 1102. The stent body 1102 may also include anchor(s) 1114A and/or 1116A. The anchor(s) 1112/1114A/1116A may be collapsible, or compressible in alternative versions of the barbed expandable stent 1100. The stent body 1002, and/or the anchor(s) 1112/1114/1116 may be compressed or held in an unexpanded state by a sheath, cover 1162, or transportation device. The sheath, cover, or transport device 1162 in one version, may be a wire or other object capable of conforming and containing the barbed expandable stent 1000 and/or stent body 1102 to or in a collapsed or unexpanded state. The sheath, cover, or transport device 1162 can include a needle 1146 attached to one end of the cover that can allow for the removal of the sheath, cover, or transport device 1162 through a vessel or other tissue.

Figure 11B:
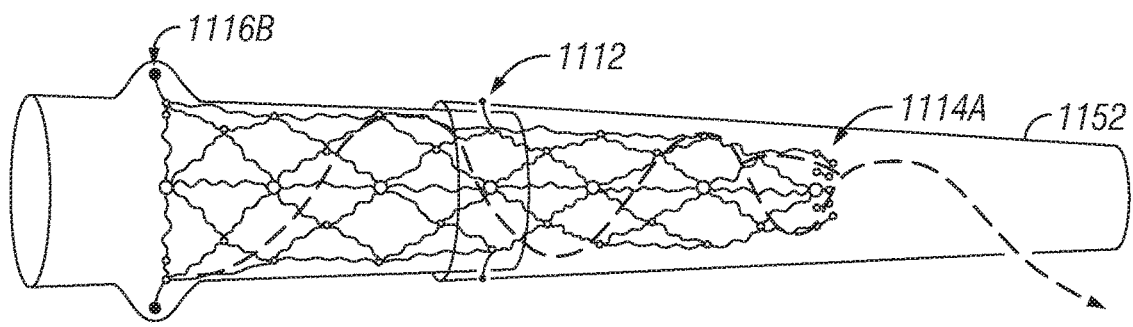
FIG. 11B is an illustration of a barbed expandable stent with donor and recipient vessel anchor(s) in a partially expanded state.

FIG. 11B is an illustration of a barbed expandable stent 1100 with donor and recipient vessel anchor(s) 1114/1116 in a partially expanded state. The anchor(s) 1116 expand or decompresses as the cover 1162 is removed, allowing the anchor(s) 1116 to engage with vessels and/or tissue. In some versions, the anchor(s) 1116 are traumatic anchor(s), where a traumatic anchor can puncture or be invasive to a vessel or tissue but would be an acceptable level of injury and/or be minimally invasive to secure the stent in place within the vessel or tissue. In other versions, the anchor(s) 1116 may be atraumatic anchor(s) that are capable of interfacing with a vessel or tissue with little to no injury or invasiveness. The radial anchor(s) 1112 may also expand, or decompress as the barbed expandable stent 1100, and/or stent body 1102 expands when the cover 1162 is removed. A recipient vessel 1152 can receive the barbed expandable stent 1100 and/or stent body 1102, with a portion of the vessel or tissue interfacing with the radial anchor(s) 1112. The needle 1146 can be utilized to remove the cover 1162 through a vessel and/or tissue, when the barbed expandable stent 1100 and/or stent body 1102 has been fully enclosed by the vessel or tissue. In at least one example, as a recipient vessel 1152 receives the stent body 1102 the needle 1146 punctures the lumen or wall of the recipient vessel 1152 to provide an exit path for the cover 1162 of the barbed expandable stent 1100.

Figure 11C:
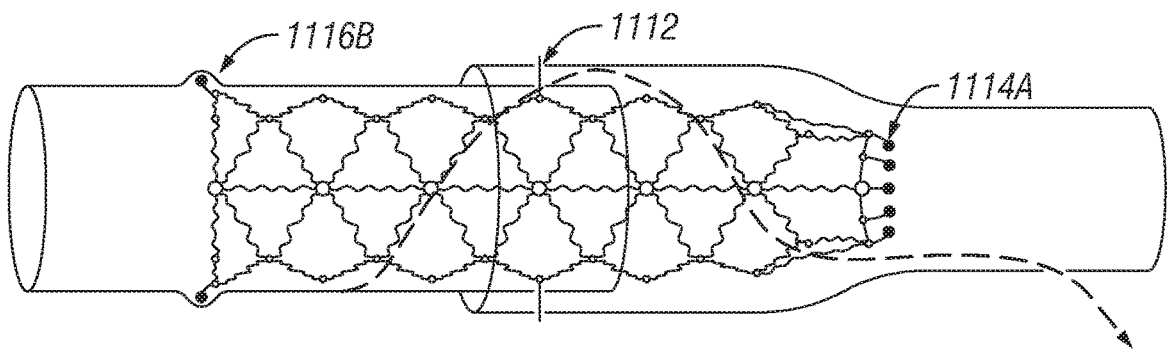
FIG. 11C is an illustration of a barbed expandable stent with donor and recipient vessel anchor(s) in a partially expanded state.

FIG. 11C is an illustration of a barbed expandable stent 1000 with donor and recipient vessel anchor(s) 1114/1116 in a partially expanded state. As the cover 1165 is removed further, additional expansion of the barbed expandable stent 1100 occurs. In one version, the barbed expandable stent 1100 interfaces with a low blood flow rate, or low pressure vessel. In a low pressure vessel, atraumatic anchor(s) can be utilized to decrease the invasiveness of the stent and/or operation. In other versions, the barbed expandable stent 1100 interfaces with a high blood flow rate, or high pressure vessel. High pressure vessels can require the use of traumatic anchor(s) to ensure that the stent does not move after it has been placed.

Figure 11D:
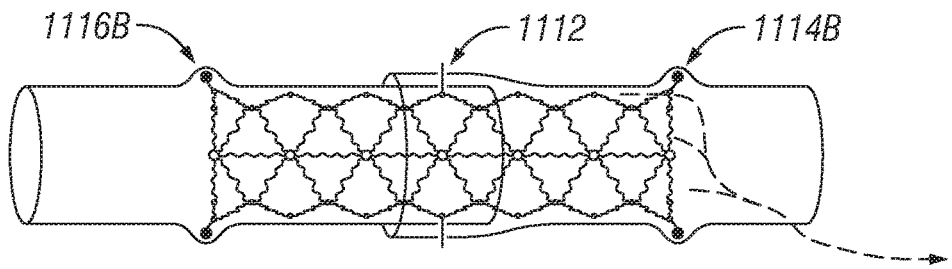
FIG. 11D is an illustration of a barbed expandable stent with donor and recipient vessel anchor(s) in an expanded state.

FIG. 11D is an illustration of a barbed expandable stent 1100 with donor and recipient vessel anchor(s) 1114/1116 in an expanded state. As the cover 1162 is removed, the anchor(s) 1114 expand or decompress allowing them to interface with a vessel or tissue. In some versions, the anchor(s) 1114 are traumatic anchor(s), where a traumatic anchor can puncture or be invasive to a vessel or tissue, where the vessel is a human vessel or mammal vessel, but would be an acceptable level of injury and/or be minimally invasive to secure the stent in place within the vessel or tissue. In other versions, the anchor(s) 1114 may be atraumatic anchor(s) that are capable of interfacing with a vessel or tissue with little to no injury or invasiveness. The radial anchor(s) 1112 may also expand, or decompress as the barbed expandable stent 1100, and/or stent body 1102 expands as the cover 1162 is removed. A recipient vessel 1152 can receive the barbed expandable stent 1100 and/or stent body 1102, with a portion of the vessel or tissue interfacing with the radial anchor(s) 1112. The cover 1162 may include multiple endings, and/or sections 1163 that can be removed with the cover 1162 and/or needle 1146. The multiple endings, and/or sections 1163 may be created by perforating or pre-perforated sections of a sheath, cover, or transport device.

Figure 12A:
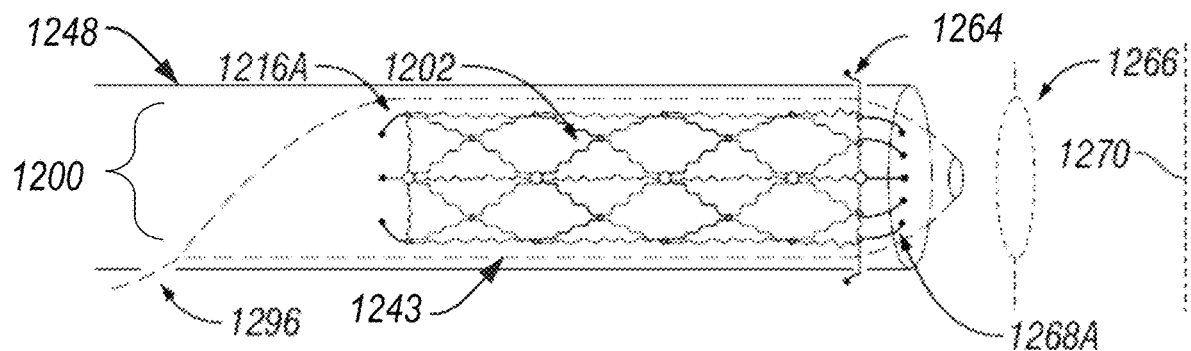
FIG. 12A is an illustration of an expandable stent for end to side anastomosis.

FIG. 12A is an illustration of an expandable stent 1200 for end to side anastomosis. The expandable stent 1200 includes a stent body 1202 and anchor(s) 1216/1264/1268. In at least one version, the expandable stent 1200 also includes a sheath, cover, or transport device 1243. The sheath, cover, or transport device 1243 may be coupled to a needle 1296 to assist in removal of the sheath, cover, or transport device 1243 after placing the expandable stent body 1202 in a proper location. In one example, the needle 1296 removes the sheath, cover, or transport device 1243 from a proximal end of the stent body 1202. A donor vessel 1248, and/or a recipient vessel 1270 can receive the expandable stent 1200.

In at least one version, the expandable stent 1200 is received by the recipient vessel 1270 through an opening 1266. In one example, a distal end of the stent body 1202 includes at least one locking anchor 1264, and at least one securing anchor 1268. The at least one locking anchor 1264, in at least one version, allows for a locking anchor(s) 1264 to bend as the expandable stent 1200 is received by the recipient vessel 1270. After the locking anchor(s) 1264 have passed the opening 1266, a spring or expansion like force will cause the locking anchor(s) 1264 to extend past the edges of the opening 1266. When the locking anchor(s) 1264 are extended past the edges of the opening 1266, a locking effect is created that prevents the expandable stent 1200 from being removed.

The at least one securing anchor 1268 can be contained and/or compressed by the sheath, cover, or transport device 1243. In at least one version, the securing anchor(s) 1268 extend through a donor vessel opening 1266, and the locking anchor(s) 1264 through the lumen(s) or wall of the donor vessel 1248.

Figure 12B:
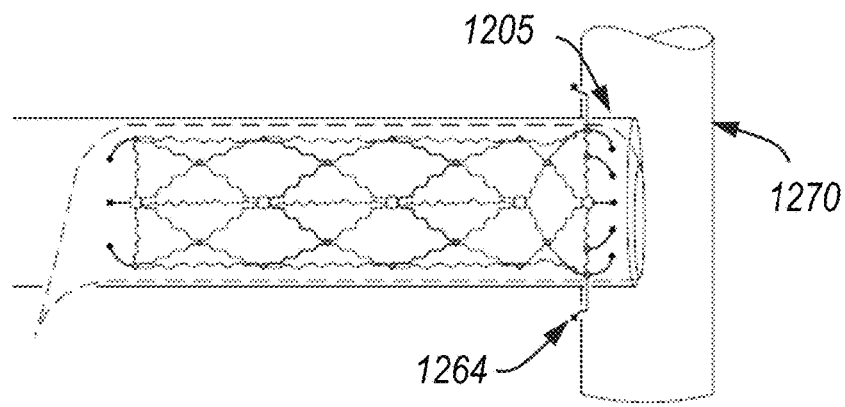
FIG. 12B is an illustration of an expandable stent for end to side anastomosis in a locked state.

FIG. 12B is an illustration of an expandable stent 1200 for end to side anastomosis in a locked state. The locked state can occur when the locking anchor(s) 1264, have passed through the opening 1266 and are interfacing 1265 with the inner lumen(s) or wall 1267 of the recipient vessel 1270. In at least one example, the locked state provides through the locking anchor(s) 1264 a resistive force that can be utilized during the removal of the sheath, cover, or transport device 1243. The needle 1246 and/or the sheath, cover, or transport device 1243 can be removed from the expandable stent 1200, and/or the stent body 1202 with some amount of force exerted on the needle 1246 and/or the sheath, cover, or transport device 1243, a counter force or resistive force can be created when the locking anchor(s) 1264 interface with the inner lumen(s) of the recipient vessel 1270. The counter force or resistive force can allow the sheath, cover, or transportation device 1243 to be separated from any points of contact with the expandable stent 1200, such as anchor(s) 1216, 1264, and/or 1268.

Until the sheath, cover, or transportation device 1243 is removed from the expandable stent 1200 the securing anchor(s) 1268 may remain contained, collapsed, and/or in an unexpanded state. With the securing anchor(s) 1268 in a contained, collapsed, and/or unexpanded state, a portion of the donor vessel 1248 is within recipient vessel 1270. In at least one example, the portion of the donor vessel 1248 within the recipient vessel 1270 can be the portion of the donor vessel 1248 between the locking anchor(s) 1264 and the distal end 1205 of the expandable stent 1200 and/or stent body 1202.

Figure 12C:
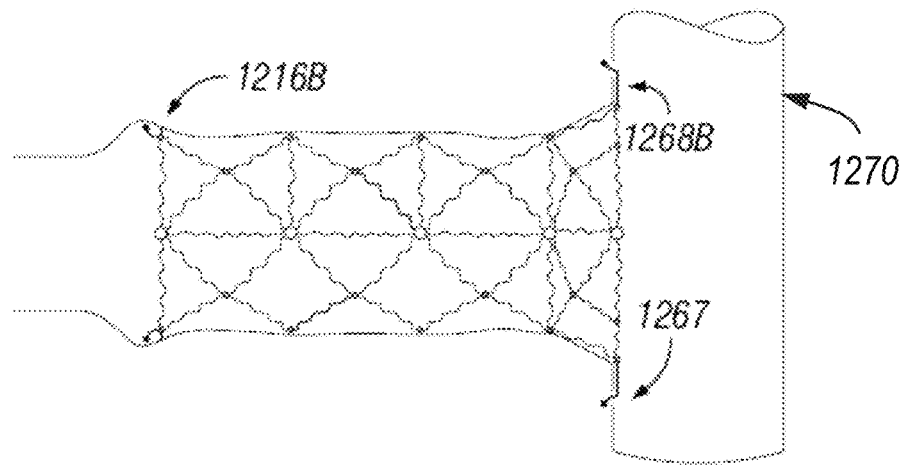
FIG. 12C is an illustration of an expandable stent for end to side anastomosis in an expanded state.

FIG. 12C is an illustration of an expandable stent 1200 for end to side anastomosis in an expanded state. The expandable stent 1200 can be expanded upon removal of the sheath, cover, or transportation device 1243. The expandable stent 1200, and/or stent body 1202 can include an expandable structure, or structure elements that may modify or expanded to match, and/or conform to the shape of the donor vessel 1248 and/or the recipient vessel 1270. In at least one example, the expandable stent 1200, and/or stent body 1202 expands the donor vessel 1248 and/or the recipient vessel 1270 beyond the respective vessel's size to allow for increased blood flow through the expandable stent 1200, stent body 1202, and/or one or both vessels 1248/1270.

The expansion can also trigger the expansion or change of state for the securing anchor(s) 1268. The expanded securing anchor(s) 1268B securing the portion of the donor vessel 1248 that is between the distal end 1205 of the expandable stent 1200, and where the locking anchor(s) 1264 have puncture or pierced the inner and/or outer lumen of the donor vessel 1248. The portion of the donor vessel 1248 can be folded over, securing and/or engaging the portion of the donor vessel 1248 against and/or over the locking anchor(s) 1264. The securing and/or engagement of the portion of the donor vessel 1248 against and/or over the locking anchor(s) 1264 creates a suturing, butterfly, and/or band aid like effect covering to prevent a loss of blood flow through the opening 1266, and/or along the edges of the opening 1266 where there is an interfacing between the donor vessel 1248 and the recipient vessel 1270.

The securing, and/or engaging the portion of the donor vessel 1248 can be assisted by an engagement and/or interfacing of the securing anchor(s) 1268B or at least one end of the securing anchor(s) 1268B with the inner lumen 1267 of the recipient vessel 1270. The securing anchor(s) 1268B and/or at least one end of the securing anchor(s) 1268B can create a seal and/or sealing effect by interfacing 1269 with the inner lumen or wall 1267 of the recipient vessel 1270. The seal and/or sealing effect can also be assisted by the portion of the donor vessel 1248 that is folded, secured and/or engaged by the securing anchor(s) 1268, against and/or over the locking anchor(s) 1264. In at least one version, the securing anchor(s) 1268B are traumatic anchor(s). In other versions, the securing anchor(s) 1268B are traumatic anchor(s) or a combination of atraumatic and traumatic anchor(s)

Figure 13A:
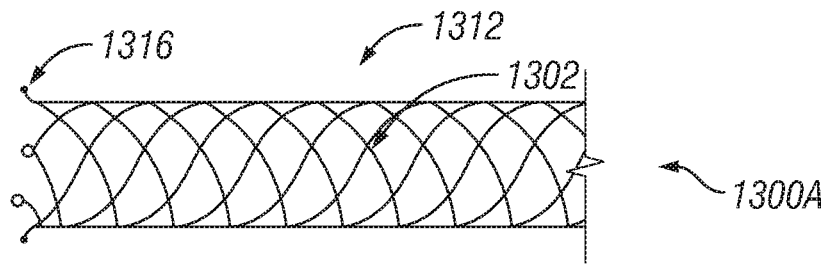
FIG. 13A is an illustration of a stent with at least one traumatic radial anchor, at least one atraumatic anchor, and at least one atraumatic anchor.
Figure 13B:
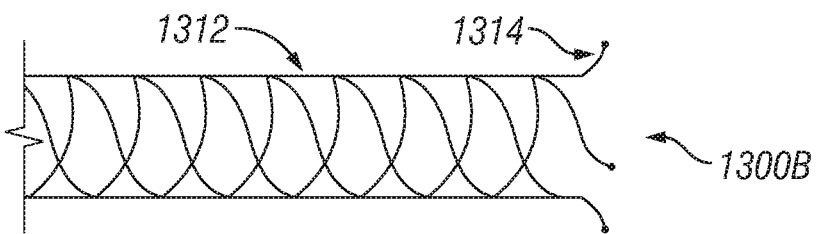
FIG. 13B is an illustration of a stent with at least one traumatic radial anchor, at least one atraumatic anchor, and at least one atraumatic anchor.
Figure 13C:
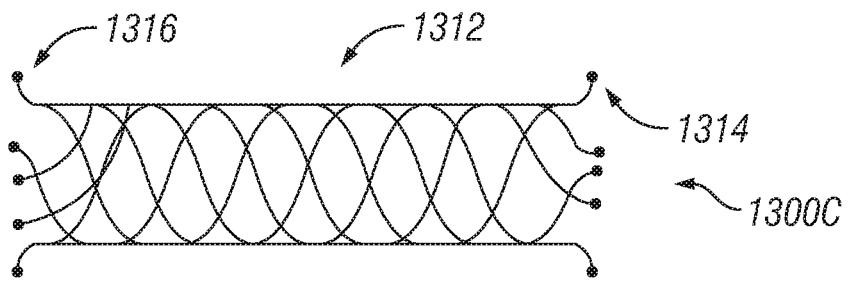
FIG. 13C is an illustration of a stent with at least one traumatic radial anchor, at least one atraumatic anchor, and at least one atraumatic anchor.

FIGS. 13A, 13B, and 13C are an illustrations of a stent 1300A, 1300B, and/or 1300C respectively with at least one traumatic radial anchor 1312, at least one atraumatic anchor 1314, and at least one atraumatic anchor 1316. The stent 1300, in one example may be an expandable stent. The expandable stent can be expanded in an accordion, twisting, and/or turning motion. In other examples, the at least one atraumatic anchor(s) 1314/1316 can be pliable and/or flexible, allowing one or both ends of the stent 1300 to be placed within a vessel (not illustrated) without an expansion, and/or delivery tool.

Figure 14A:
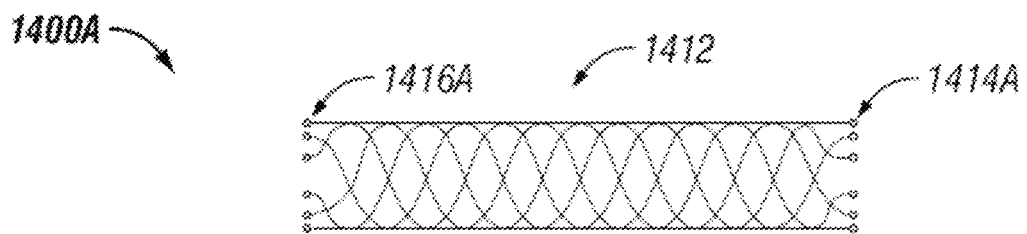
FIG. 14A is an illustration of an expandable stent with traumatic and atraumatic anchor points in an unexpanded state.

FIG. 14A is an illustration of an expandable stent 1400A with traumatic and atraumatic anchor points in an unexpanded state. The expandable stent 1400A includes at least one traumatic anchor 1416, and/or at least one atraumatic anchor 1414. The anchor(s) 1414/1416, in alternative examples, may both be traumatic, or atraumatic anchor(s). The anchor(s) 1414/1416, in at least one version, are expandable allowing for a change from an unexpanded state to an expanded or extended state. The expansion in one example, may be from the material utilized to manufacture the expandable stent 1400A and/or the anchor(s) 1414/1416. In other examples, the expansion may be the result of the flexibility, or other outside forces on the anchor(s) 1414/1416. In at least one version, the anchor(s) 1414/1416 may be contained and/or collapsed by a sheath, cover, or transport device (not illustrated). In alternative versions, the anchor(s) 1414/1416 may be expanded, or change states based on an expansion of the expandable stent 1400A. For example, the anchor(s) 1414/1416 may transition based on a pulling or tightening effect that is triggered by the expansion of the expandable stent 1400A. The pulling or tightening effect can cause the anchor(s) 1414/1416 to expand or transition outward from a position parallel to, or in a plane parallel to the stent body, to a position or expanded state that is diagonal or perpendicular to the stent body and/or a plane parallel to the stent body. The expandable stent 1400A can also include at least one radial anchor 1412 that extends radially from the expandable stent 1400A and/or stent body. In at least one version, the radial anchor(s) 1412 are expandable and/or collapsible.

Figure 14B:
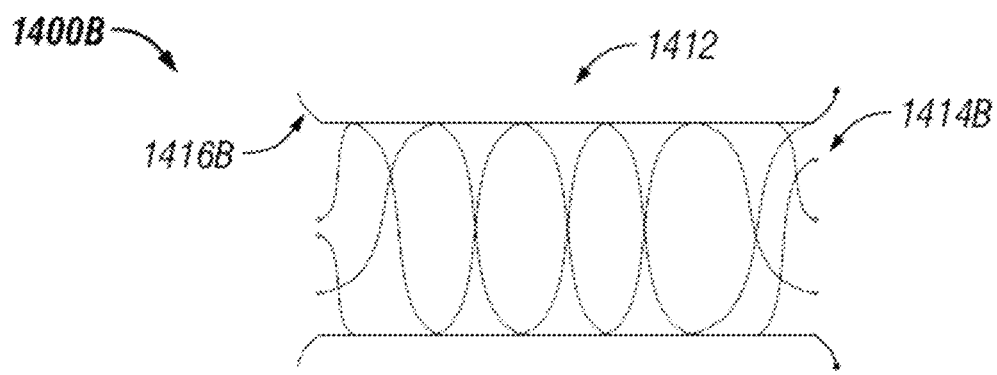
FIG. 14B is an illustration of an expandable stent with traumatic and atraumatic anchor points in an expanded state.

FIG. 14B is an illustration of an expandable stent 1400B with traumatic and atraumatic anchor points in an expanded state. The expandable stent 1400B can transition from an unexpanded state to an expanded state, in both a radial (outwardly along the circumference of the stent body 1402) and/or linearly (outwardly from a proximal end 1403 and/or a distal end 1405 of the expandable stent 1400B). During a radial manner expansion, the anchor(s) 1414/1416 can extend and/or decompress based on a tensioning and/or repulsion force that causes the anchor(s) 1414/1416 to extend in an upward and/or outwardly manner from the expandable stent 1400A and/or stent body 1402. In a linear manner expansion, a tensioning and/or repulsion force that causes the anchor(s) 1414/1416 to extend in an upward and/or outwardly manner from the expandable stent 1400A and/or stent body 1402. The linear, and/or radial expansion can allow the anchor(s) 1412/1414/1416 to interface and/or engage with vessel(s) and/or tissue.

Figure 15:
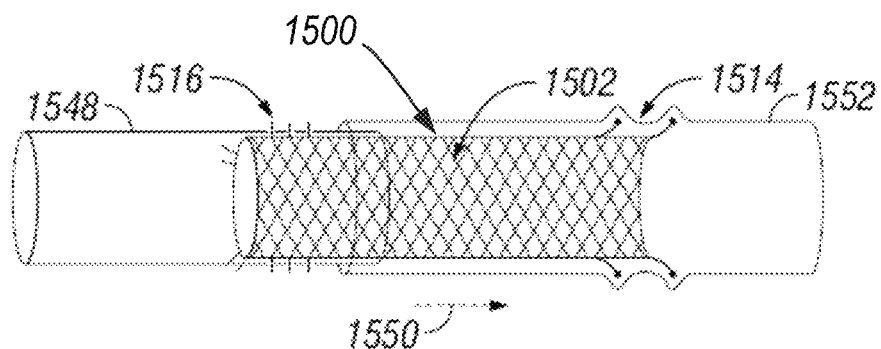
FIG. 15 is an illustration of an expandable stent with traumatic and atraumatic anchor points attached to donor and recipient vessels.

FIG. 15 is an illustration of an expandable stent 1500 with traumatic and atraumatic anchor points attached to donor and recipient vessels. The expandable stent 1500 can include at least one atraumatic anchor 1514 and at least one traumatic anchor 1516. The anchor(s) 1514/1516 can be expandable and/or compressible allowing them to be expanded and/or compressed along with the expandable stent 1500.

In at least one version, the expandable stent 1500 is manufactured of a material that is reactive. The reactive material, can react to a blood flow 1550, initiating an expansion of the expandable stent 1500. In other versions, the reactive material, could react to a magnetic or electrical field or code that can trigger an expansion.

The expandable stent 1500 can be placed in a high pressure vessel that has a blood flow 1550 rate that can cause a stent to move if it is not secured. In at least one version, the expandable stent 1500 is secured by the traumatic anchor(s) 1516, and/or the atraumatic anchor(s) 1514. For example, in a high pressure or high blood flow rate vessel the traumatic anchor(s) 1516 can be used. In other examples, such as a low pressure or low blood flow rate vessel the atraumatic anchor(s) 1514 can be used. Still in other examples, a combination of traumatic and atraumatic anchor (s) may be utilized to allow the stent to utilize traumatic anchor(s) on the vessel transmitting and/or transferring a blood flow such as a donor vessel 1548, and atraumatic anchor(s) on with the vessel receiving a blood flow, such as a recipient vessel 1552.

Figure 16:
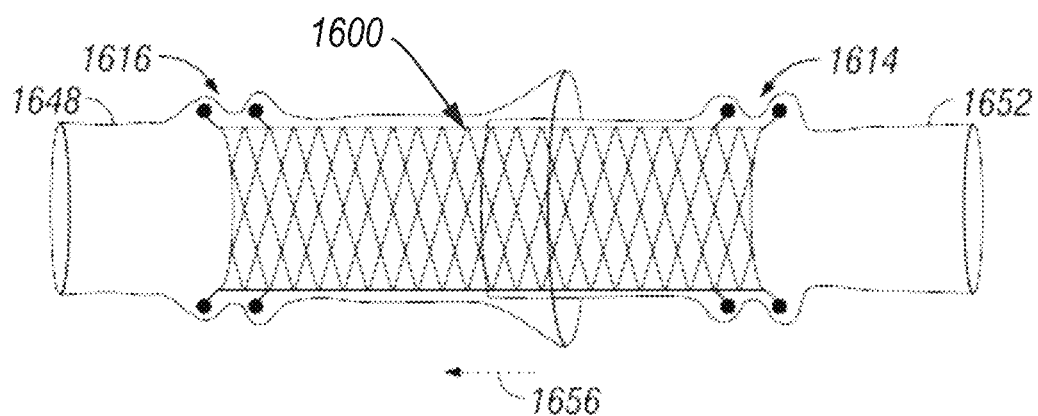
FIG. 16 is an illustration of an expandable stent with a plurality of atraumatic anchor(s).

FIG. 16 is an illustration of an expandable stent 1600 with a plurality of atraumatic anchor(s) 1672A/1672B/1672C/1672D/1672E (collectively 1672). In at least one version of the expandable stent 1600, the stent body 1602 can include a plurality of atraumatic anchor(s) 1672 along the circumference of the expandable stent. The anchor(s) 1672, can in alternative versions be traumatic anchor(s). In at least one example, the anchor(s) 1672 are collapsible and/or compressible. The expandable stent 1600, can be covered and/or protected by a sheath, cover, transport, and/or delivery device (not illustrated). The sheath, cover, transport, and/or delivery device (not illustrated) can provide for a force that contains, collapses, and/or compresses the anchor(s) 1672.

Figure 17:
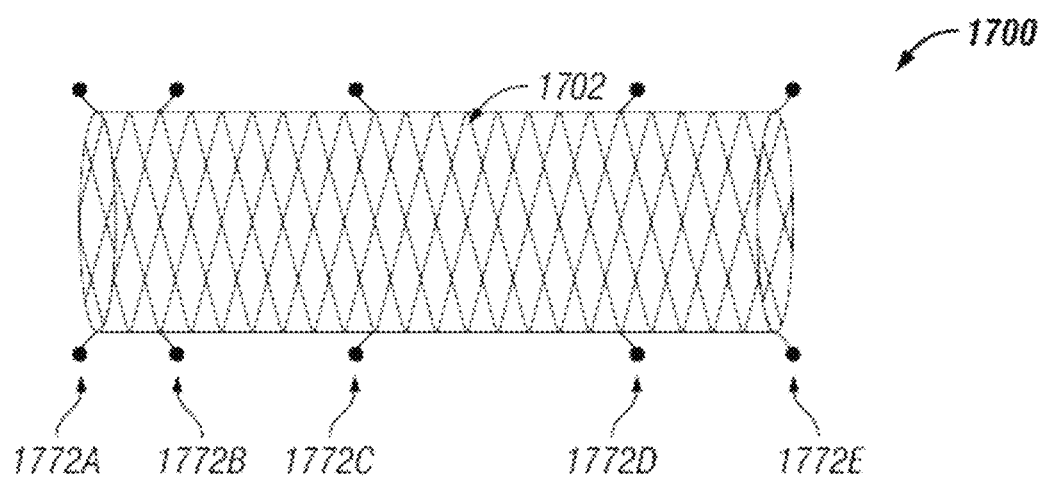
FIG. 17 is an illustration of an expandable stent with a plurality of atraumatic anchor(s).

FIG. 17 is an illustration that stent 1700. The stent 1700 can include a plurality of anchor points 1772A, 1772B, 1772C, 1772D, and/or 1772E. In at least one example the anchor points 1772 (collectively) may be atraumatic anchor points. The stent body 1702 may also be expandable and/or collapsible. In at least one embodiment, the atraumatic anchor points can allow for the securing of the stent 1700 in a low flow, and/or low pressure vessel. In at least one example, the anchor points may allow for a securing of a vessel to the stent apparatus, and may also be compressible.

While this invention has been particularly shown and described with reference to preferred embodiments, it will be understood by those skilled in the art that various changes in form and detail may be made therein without departing from the spirit and scope of the invention. The inventors expect skilled artisans to employ such variations as appropriate, and the inventors intend the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

While various embodiments in accordance with the principles disclosed herein have been described above, it should be understood that they have been presented by way of example only, and not limitation. Thus, the breadth and scope of this disclosure should not be limited by any of the above-described exemplary embodiments, but should be defined only in accordance with any claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, and by way of example, although the headings refer to a "Technical Field," the claims should not be limited by the language chosen under this heading to describe the so-called field. Further, a description of a technology as background information is not to be construed as an admission that certain technology is prior art to any embodiment(s) in this disclosure. Neither is the "Brief Summary of the Invention" to be considered as a characterization of the embodiment(s) set forth in issued claims. Furthermore, any reference in this disclosure to "invention" in the singular should not be used to argue that there is only a single point of novelty in this disclosure. Multiple embodiments may be set forth according to the limitations of the multiple claims issuing from this disclosure, and such claims accordingly define the embodiment(s), and their equivalents, that are protected thereby. In all instances, the scope of such claims shall be considered on their own merits in light of this disclosure, but should not be constrained by the headings set forth herein.

I claim:

1. A stent apparatus for use in surgical applications, comprising:
    (a) a single hollow tubular section with a proximal end for engaging with a first vessel and a distal end for engaging with a second vessel to fluidly couple the first vessel and the second vessel together at an overlap area through anastomoses;
    (b) a plurality of outwardly extending radial anchor points located between the proximal end and the distal end for engaging at least one of the first vessel and the second vessel in the overlap region;
    (c) a compression material over the stent apparatus compressing the stent apparatus; and
    wherein the compression material is removable from the stent apparatus permitting expansion of the stent apparatus and thereby the plurality of radial anchor points; and
    wherein the hollow tubular section comprises a mesh of nodes and interconnected elements having expansion memory.

2. The stent apparatus of claim 1, further comprising:
    (d) at least one set of atraumatic anchors located at either the proximal end or the distal end.

3. The stent apparatus of claim 1, wherein the hollow tubular section is 3D printed.

4. The stent apparatus of claim 1, wherein the plurality of radial anchor points is atraumatic to a human vessel.

5. The stent apparatus of claim 1, wherein the plurality of radial anchor points includes means for securing a vessel to the stent apparatus.

6. The stent apparatus of claim 1, wherein the plurality of radial anchor points is deflected from a first orientation by the compression material, wherein the first orientation is flattened against the stent apparatus.

7. The stent apparatus of claim 1, wherein the plurality of radial anchor points is deflected from a first orientation by the compression material, wherein the first orientation is collapsed against the stent apparatus.

8. The stent apparatus of claim 1, wherein the stent apparatus further comprises at least one compressible securing anchor point at each of the proximal end and the distal end of the hollow tubular section that respectively pierce an endoluminal surface of the first and second vessels during the anastomoses.

9. The stent apparatus of claim 8, wherein the proximal end of the hollow tubular section further comprises a distal end section for interfacing with a human vessel, an attachment end section, and a proximal end section that connects to the hollow tubular section.

10. The stent apparatus of claim 9, wherein the distal end section further comprises a plurality of said at least one securing anchor points.

11. The stent apparatus of claim 9, wherein the attachment end section further comprises a plurality of said at least one securing anchor points.

12. The stent apparatus of claim 9, wherein the proximal end section further comprises a plurality of said at least one securing anchor points.

13. The stent apparatus of claim 1, wherein the distal end of the hollow tubular section further comprises at least one compressible securing anchor point that pierces an endoluminal surface of either the first or second vessel during the anastomoses, and wherein the distal end further comprises a distal end section for interfacing with a human vessel, an attachment end section, and a proximal end section that connects to the hollow tubular section.

14. The stent apparatus of claim 13, wherein the distal end section further comprises said at least one compressible securing anchor point.

15. The stent apparatus of claim 13, wherein the attachment end section further comprises said at least one compressible securing anchor point.

16. The stent apparatus of claim 13, wherein the proximal end section further comprises said at least one compressible secure anchor point.

17. The stent apparatus of claim 13, wherein said at least one compressible securing anchor point is atraumatic to a human vessel.

18. The stent apparatus of claim 13, wherein said at least one compressible securing anchor point is positioned in a radial manner around a circumference of the hollow tubular section.

19. The stent apparatus of claim 1, wherein said at least one compressible securing anchor point is positioned in a linear manner along a length of the hollow tubular section.

20. The stent apparatus of claim 1, wherein the interconnected elements of the hollow tubular section are cylindrical.

* * * * *